United States Patent
Hennings et al.

(10) Patent No.: US 8,430,104 B2
(45) Date of Patent: Apr. 30, 2013

(54) METHOD FOR TREATMENT OF MICROBIAL INFECTION

(75) Inventors: David R. Hennings, Roseville, CA (US); Guillermo-Mendoza Aguilar, Roseville, CA (US)

(73) Assignee: CoolTouch Incorporated, Roseville, CA (US)

( * ) Notice: Subject to any disclaimer, the term of this patent is extended or adjusted under 35 U.S.C. 154(b) by 245 days.

(21) Appl. No.: 12/902,843

(22) Filed: Oct. 12, 2010

(65) Prior Publication Data

US 2011/0144564 A1 Jun. 16, 2011

Related U.S. Application Data

(63) Continuation-in-part of application No. 11/466,047, filed on Aug. 21, 2006, now abandoned, which is a continuation of application No. 09/934,356, filed on Aug. 21, 2001, now Pat. No. 7,094,252.

(51) Int. Cl.
*A61B 19/00* (2006.01)
*A61F 7/00* (2006.01)

(52) U.S. Cl.
USPC .............. 128/898; 607/89; 607/88; 607/100; 604/20

(58) Field of Classification Search .............. 607/88–91, 607/96, 100, 102, 104, 111; 606/3, 9, 13–18; 604/19, 20; 128/898
See application file for complete search history.

(56) References Cited

U.S. PATENT DOCUMENTS 7,494,503 B2 * 2/2009 McDaniel ...................... 607/88
7,918,229 B2 * 4/2011 Cumbie et al. ................ 128/898

* cited by examiner

*Primary Examiner* — Ahmed Farah
(74) *Attorney, Agent, or Firm* — Ray K. Shahani, Esq.; Kin Hung Lai

(57) ABSTRACT

A method and apparatus for treatment of skin or other tissue, using a source of thermal, electromagnetic radiation, electrical current, ultrasonic, mechanical or other type of energy, to cause minimally-invasive thermally-mediated effects in skin or other tissue which stimulates a wound-healing response, in conjunction with topical agents or other wound healing compositions, for application on the skin or other tissue which accelerate collagenesis, such as in response to wound healing. The dosage and time period of application of the compositions are adjusted to prevent external or surface tissue damage.

15 Claims, 20 Drawing Sheets

METHOD FOR TREATMENT OF MICROBIAL INFECTION

RELATED APPLICATIONS

This application is a Continuation-In-Part of pending U.S. patent application Ser. No. 11/466,047 filed Aug. 21, 2006 now abandoned entitled ENHANCED NONINVASIVE COLLAGEN REMODELING, which is a Continuation of U.S. patent application Ser. No. 09/934,356 filed Aug. 21, 2001 and issued Aug. 22, 2006, U.S. Pat. No. 7,094,252 entitled ENHANCED NONINVASIVE COLLAGEN REMODELING, which is incorporated herein by reference in its entirety, and claims any and all benefits to which it is entitled therefrom. This application is also related to pending U.S. patent application Ser. No. 12/841,110 filed Jul. 12, 2010 entitled TREATMENT OF MICROBIAL INFECTIONS USING HOT AND COLD THERMAL SHOCK AND PRESSURE, which is a Non-Provisional application related to pending U.S. Provisional Patent Application Ser. No. 61/227,739 filed Jul. 22, 2009 entitled TREATMENT OF MICROBIAL INFECTIONS USING HOT AND COLD THERMAL SHOCK AND PRESSURE, which is incorporated herein by reference in its entirety, and claims any and all benefits to which it is entitled therefrom.

FIELD OF THE INVENTION

This invention is related to the controlled delivery of photothermal or other type of energy for treatment of biological or other tissue, and more specifically, a method, system and kit for causing a subdermal wound such that further repair and healing improvement of tissue is accelerated. This invention also relates to the treatment and inactivation of microbial infections, in particular fungal infections of the toenail by sequentially applying a source of thermal energy to the nail bed and then applying cold to the infected location to inactivate the microbe. This "thermal shock" therapy is more efficient, safer, and more effective than previous methods of using either thermal or cryogenic cold separately.

BACKGROUND OF THE INVENTION

Previous disclosures, such as U.S. Pat. No. 4,976,799 and U.S. Pat. No. 5,137,539 have described methods and apparatus for achieving controlled shrinkage of collagen tissue. These prior inventions have applications to collagen shrinkage in many parts of the body and describe specific references to the cosmetic and therapeutic contraction of collagen connective tissue within the skin. In the early 1980's it was found that by matching appropriate laser exposure parameters with these conditions, one had a novel process for the nondestructive thermal modification of collagen connective tissue within the human body to provide beneficial changes. The first clinical application of the process was for the non-destructive modification of the radius of curvature of the cornea of the eye to correct refractive errors, such as myopia, hyperopia, astigmatism and presbyopia. New studies of this process for the previously unobtainable tightening of the tympanic membrane or ear drum for one type of deafness have been made.

$CO_2$ laser resurfacing is not a new technique. $CO_2$ lasers have been used for several years, but regular continuous wave $CO_2$ lasers can cause scarring due to the tissue destruction caused as heat as conducted to adjacent tissue. Even superpulse $CO_2$ lasers produce excessive thermal damage. The Ultrapulse $CO_2$ laser introduced by Coherent, Inc. is an attempt to assuage these drawbacks by offering a high energy, short duration pulse waveform limiting the damage to less than 50 microns allowing a char-free, layer by layer vaporization of the skin tissue.

All of the foregoing procedures depend for their success upon primary damage and the reparative potential induced by the inflammatory process in the tissue. Associated with inflammation are, of course, the four cardinal signs of inflammation of rubor (hyperemia), calor (thermal response), dolor (pain), and tumor or edema or swelling. Coincident with these manifestations is the risk of reduced resistance to infection. One must not forget that these collateral effects accompany a cosmetic enhancement procedure and, for the most part, are not associated with a therapeutic procedure. Therefore, the development of a more efficacious method would be beneficial in this regard.

U.S. Pat. Nos. 4,976,709, 5,137,530, 5,304,169, 5,374,265, 5,484,432 issued to Sand, disclose a method and apparatus for controlled thermal shrinkage of collagen fibers in the cornea using light at wavelengths between 1.8 and 2.55 microns. However strong absorption of the laser energy by water limits the penetration depth to the most superficial layers of skin.

The CoolTouch™ 130 laser system by CoolTouch Corp of Auburn, Calif., was first introduced at the Beverly Hills Eyelid Symposium in 1995. It utilizes a laser at a wavelength of 1.32 microns to cause thermally mediated skin treatment. In this device the treatment energy is targeted at the surface of the skin with in depth optical heating of the epidermis, papillary dermis, and upper reticular dermis. The energy is primarily absorbed in tissue water with a skin absorption coefficient of 1.4 cm−1, corresponding to an absorption depth of 0.71 cm. Scattering of the 1.32 micron wavelength light by skin microstructures alters the distribution of light from an exponential attenuation to a more complex distribution, which has much faster attenuation approximating an absorption depth of 0.1 cm. Most of the energy is absorbed in the first 250 microns of tissue. To prevent overheating of the epidermis pulsed cryogen spray precooling is used. U.S. Pat. No. 5,814,040, issued Sep. 29, 1998, describes a dynamic cooling method utilizing pulsed cryogen spray precooling. Skin treated with this device has improved texture and a reduction in wrinkles and scarring due to the long term renewal of dermal collagen without significant skin surface wounding.

U.S. Pat. No. 5,810,801 teaches a method and apparatus for treating a wrinkle in skin by targeting tissue at a level between 100 microns and 1.2 millimeters below the surface, to thermally injure collagen without erythema, by using light at wavelengths between 1.3 and 1.8 microns. The parameters of the invention are such that the radiation is maximally absorbed in the targeted region. The invention offers a detailed description of targeting the 100 micron to 1.2 mm region by utilization of a lens to focus the treatment energy to a depth of 750 microns below the surface. Because of the high scattering and absorption coefficients, precooling is utilized to prevent excess heat build up in the epidermis when targeting the region of 100 microns to 1.2 mm below the surface. The wavelength range of use is 1.3 microns to 1.8 microns in order to avoid the wavelength range of Sand. However the wavelength range of 1.4 to 1.54 microns and the range between 2.06 and 2.2 microns have identical effective attenuation coefficients in skin. Also the range from 1.15 to 1.32 microns has a fairly uniform effective attenuation coefficient in skin of about 6 to 7 $cm^{-1}$. The effective attenuation length in skin for the range of wavelengths of 1.3 to 1.8 microns varies from 6 $cm^{-1}$ at 1.3 microns to 52 $cm^{-1}$ microns, corresponding to penetration depths in skin of 200 microns to 2 millimeters. Specific laser and cooling parameters are selected so as to avoid erythema and achieve improvement in wrinkles as the long term result of a new collagen formation following treatment.

Mucini et al. reported effective dermal remodeling using a 980 nm diode laser with a spherical handpiece which focused irradiation into the dermis avoiding the high scattering and absorption characteristic of longer wavelengths. The device requires a small lens of a few millimeters in contact with skin and results in a slow procedure when used for facial areas.

Ross et al., reported the use of an Erbium:YAG laser operating at a wavelength of 1.54 microns fired in a multiple pulsed mode has been described for eliciting changes in photodamaged skin A chilled lens in contact with skin at the treatment site was used in an attempt to spare the epidermis. Treatment occurred during a period of several seconds with a sequence of cooling and heating with the laser and handpiece. At 1.54 microns the optical penetration depth 0.55 mm and the authors reported that the surface must be chilled before the laser exposure requiring a complex method of cooling and laser exposure. The authors state that a more superficial thermal injury may be needed than could be achieved, and that there are increased patient risks because it would demand more accurate and precise control of heating and cooling.

Bjerring et al, reported the use of a visible light laser, operating at 585 nm wavelength, to initiate collagenesis following interaction of laser energy with small blood vessels in skin.

As many as 700 million people worldwide suffer from onychomycosis or toenail fungal infections. There are many systemic, topical and herbal treatments available to treat this disease but none are truly efficacious and several have severe potential side effects. A need exists for a better cure for this widespread disease.

Optical and laser treatment of toenail fungus has been known for many years. In particular, UV light in the 100-400 nm range has proven to be able to inactivate many pathogens including the ones responsible for onychomycosis in non-thermal dosages. Unfortunately UV light has difficulty penetrating the toenail and can cause side effects in the dermis. UV light is not considered to be a successful treatment modality despite a great deal of research.

U.S. Pat. No. 6,723,090, issued Apr. 20, 2004 to Altshuler et al., U.S. Pat. No. 7,220,254, issued May 22, 2007 to Altshuler et al., US Publication No. 2006/0212098, published Sep. 21, 2006 to Demetriou et al., Non-patent publication "Laser treatment for toenail fungus", Proc. of SPIE Vol. 7161 published 2009 by Harris et al. and others have proposed using infrared radiation to thermally inactivate toenail fungus. Infrared radiation penetrates the toenail much better than UV and it has been shown that the fungus can be inactivated by raising the temperature of the pathogen to about 50° C. The problem associated with this method is that achieving the inactivation temperature in the nail bed risks damaging the surrounding dermal tissue, especially the matrix where the nail actually grows. In addition this prior art allows the use of infrared radiation with high hemoglobin absorption. Hemoglobin absorbing wavelengths can coagulate capillaries in the proximal fold and permanently damage the toenail.

U.S. Pat. No. 6,723,090, issued Apr. 20, 2004 to Altshuler et al., U.S. Pat. No. 7,220,254, issued May 22, 2007 to Altshuler et al. propose to use a cooling modality to protect the toenail during infrared laser irradiation to target the nail bed and he suggests that a pulsed laser may be superior to a continuous one.

US Publication No. 2006/0212098, published Sep. 21, 2006 to Demetriou et al. suggests the use of pulsed cryogen cooling, which is also described in U.S. Pat. No. 5,814,040, issued Sep. 29, 1998 to Nelson et al., to protect the toe from excessive heating and to use the process of selective photothermolysis, which is disclosed in non-patent publication "Selective Photothermolysis: Precise Microsurgery by Selective Absorption of Pulsed Radiation", published on Science, 220:524-527, 1983 by Anderson et al., to choose the correct pulse length to match the thermal properties of the fungus itself. Methods taught respectively in U.S. patent '090, '254 to Altshuler et al. and US Publication '098 by Demetriou et al. all require relatively high target temperatures that can damage the matrix and teach to cool only the surrounding tissue. The above-mentioned methods may cause permanent damage to sensitive areas.

U.S. Pat. No. 6,090,788, issued Jul. 18, 2000 to Lurie teaches that light-absorbing substances may be considered to induce and enhance selective photothermal damage. The problem and shortcoming with this method is the difficulty in getting the substance infused to the proper areas and the high temperatures required to inactivate the microbe. Damage to the surrounding tissue is likely to happen by using this method.

Non-patent publication "Method for disruption and re-canalization of atherosclerotic plaques in coronary vessels with photothermal bubbles generated around gold nanoparticles", published on Lasers Surg Med, 2009. 41(3): p. 240-7 by Lukianova-Hleb, E. Y., A. G. Mrochek, and D. O. proposes a non-thermal mechanical and localized removal of plaque tissue with photothermal microbubbles—PTMB to re-canalize occluded arteries without collateral damage using gold nano particles—GNP. It also teaches that users can induce non-thermal damage to locally remove unwanted tissue by producing PTMB using GNP as a catalyzer. This method however has not been proven to be efficient enough to be practical in removing large volumes of plaque buildup.

Non-patent publication "Laser surgery of port wine stains using local vacuum pressure: Changes in skin morphology and optical properties (Part I)", published on Lasers Surg Med, 2007. 39(2): p. 108-17 by Childers et al. proposes that mild vacuum pressures applied to the skin surface causes changes in morphology and its optical properties. These changes may be used for more efficient photothermolysis of small Port Wine Stain blood vessels. The vacuum suggested by Childers et al. however works primarily on blood vessels in the dermis.

OBJECTS AND ADVANTAGES OF THE PRESENT INVENTION

The object of this invention is to provide a method and device for improving skin by treating layers of skin without damaging the surface or deep skin layers. It is another object of this invention to provide a method and device for improving acne scars or photodamaged skin without causing a surface injury to skin It is another object of this invention to provide a method and device for accelerating the collagenesis after treating skin without damaging the surface of skin.

The present invention circumvents the problems of the prior art and provides a system for achieving erythema and mild edema in an upper layer of skin without the risk of high fluence levels or surface wounds. The invention offer advantages over existing devices by allowing the use of lower fluence levels resulting in faster treatments and less cost. Collagen remodeling is induced by distributing the therapeutic energy over a series of more benign treatments spaced weeks apart.

Numerous other advantages and features of the present invention will become readily apparent from the following detailed description of the invention and the embodiments thereof, from the claims and from the accompanying drawings.

The present invention is a method and apparatus for skin or other tissue treatment, using a source of thermal energy, which may be electromagnetic radiation, electrical current, or ultrasonic energy, to cause minimal-invasive thermally-mediated effects in skin, nail or other tissue leading to a wound-healing, immune response, in conjunction with topical agents which accelerate collagenesis in response to wound healing or topical agents such as an anti-microbial agent applied directly to the top of the toenail prior to, subsequent to or concurrently with treatment. One aspect of the wound healing response accompanying treatment with electromagnetic energy to heat tissue is stimulation of the immune system or natural ability of the body to fight pathogens and/or disease, including but not limited to viruses and fungii. The dosage and time period of application are adjusted to prevent external or surface tissue damage.

The present invention makes the treatment of microbial infections much more effective and efficient than previously taught in the prior art. The present invention is also a method for treatment of microbial infection of human skin, the method comprising treating a subsurface layer of virus infected skin with a source of electromagnetic energy sufficient to cause stimulation of an immune response without thermal damage to the epidermis, in conjunction with applying an anti-microbial agent directly to the upper surface of the dermis, thereby improving treatment efficiency, particularly where the infection is a viral infection such as a wart.

Target thermal feedback has been used in the prior art, such as in the laser treatment devices of Koop et al., but has not been considered in the treatment of onychomycosis or other fungal or microbial infections because of the difficulty of obtaining consistent thermal readings from low emissivity targets like a toenail. Since the toenail has a very low water content, its emissivity is much lower than the dermis. Therefore, it has been unexpectedly found that use of a thermal sensor designed to work on tissue would also work on the toenail. It would not be obvious that a correlation between the surface temperature of the nail and the nail bed exists or that the thermal response time of the detector can be made fast enough to control a laser to prevent overheating of the tissue. Nor would it be obvious that thermal feedback can be made to work in a sequential mode with aggressive cooling fluids such as but not limited to cold air, chilled water, refrigerant and/or cryogen spray cooling. It is not obvious that a thermal detector can also measure and control cooling. Automatic target thermal feedback prevents over or under treatment that is inherent in the prior art.

The present invention uses the process of thermal shock to help inactivate the fungus. Either heat or cold by themselves are effective at inactivating pathogens but rapid changes of temperature are even more effective in inactivating pathogens and are more tolerable by surrounding tissue. The present invention therefore uses rapid cooling to cool the target tissue followed by rapid heating of the target tissue or vice versa. Prior art teaches against cooling the target tissue because it then takes much more thermal energy to overcome the cold and heat the target to effective temperatures. Prior art teaches to only cool surrounding or overlaying tissue and to avoid cooling the pathogen itself or the target area. This is because prior art assumes the target tissue damage has to be induced by high temperatures and cooling is only an auxiliary procedure to prevent excessive heating. Our invention inactivates the pathogen with low and high extreme temperatures far more effectively and efficiently than the use of either one alone, thus making the procedure much more efficient and safer. It also allows for a temporary change of mechanical, thermal and optical properties, e.g., as the fungus freezes during a pre-cooling procedure it turns icy which results in more scattering, which makes it more susceptible to absorption from the subsequent laser irradiation in the visible and IR spectra and also more brittle, which also makes it more susceptible to subsequent mechanical deformation. This invention will inactivate microbes at lower heating temperatures making it safer and less painful than prior art.

The present invention uses mechanical deformation, such as induced by mechanical pressure, to disrupt mechanically the fungal bed once it has been frozen. Cooling in the form of a spray onto the target nail surface works optimally in conjunction with steady or pulsed infrared laser irradiation with a pulse length chosen to be selectively absorbed by the fungus. No prior art has suggested that cold application be used therapeutically to inactivate microbes. This invention will allow the inactivation of microbes with less energy applied causing less pain and chance of damage to surrounding tissue.

The present invention uses localized and temporary external vacuum pressure through the use of a transparent toe jacket. This jacket seals around the toe and is instrumented with a vacuum pump to lower the atmospheric pressure around it, optionally including the toenail-fungus-toe space, prior to treatment. By doing so, the boiling temperature of either the existing moisture within the fungus bed or of a previously diffused water-based solution is diminished proportionally, requiring the use of lower laser fluences, but most importantly, inducing evaporation, bubble growth and subsequent bubble explosion at temperatures much lower than the threshold of tissue damage and patient pain. In fact, depending on the absolute vacuum pressure that one can achieve within the jacket, this procedure may induce the formation of cavitation bubbles underneath the toenail with minimal or even without the need for laser heating, e.g., IPL. Thus, this combined mechanism adds the potential of inducing localized mechanical ablation to the thermal ablation induced by the laser or IPL. This invention allows the inactivation of microbes with much less energy applied making it more effective and safer.

The present invention adds highly absorbing dyes and/or metallic nanoparticles such as gold nanoparticles GNP to enhance the absorption by the targeted fungus. This approach also benefits from the combined application of vacuum pressure to induce cavitation and lower the threshold for nucleation of evaporation bubbles and thus the temperature of the treated area. Furthermore, the use of GNP causes photothermal micro-bubbles PTMB at the surface of the GNP, which in turn provide an effective way of promoting non-thermal mechanical and localized inactivation of microbes. Prior art has not taught the use of GNP to inactivate living microbes. Prior art has only utilized GNP to physically ablate nonliving tissue such as plaque.

The present invention uses positive pressure on the toe or toe nail against each other with the objective to temporarily "blanch" the subjacent skin from blood supply. The intent is to temporarily remove blood perfusion to this region and thus reduce the concentration of competing absorbers, i.e., hemoglobin, for the subsequent laser or IPL irradiation. This "blanching" effect occurs within the first 0.5 sec after pressure is applied onto the skin After that time, blood perfusion returns and even increases within that region. Depending on the wavelength(s) used for this purpose, it is beneficial to the procedure to wait longer than 0.5 sec to have a back absorber underneath the fungus bed which can serve as a heat source for prolonged heating of the fungus. This invention will reduce the energy needed to inactivate the microbe making the procedure much safer and more effective. Prior art does not teach to cycle the pressure on the target. The use of positive pressure will force the blood out of small capillaries in the matrix of the nail. Lasers and energy sources with wavelengths that are absorbed in hemoglobin such as those from Intense pulsed light systems and lasers with wavelengths in the visible and near infrared from 400 nm to 1100 nm can then be safely used, and when treating only the nail bed the subsequent perfusion will enhance the energy absorption in this area resulting in a more efficient treatment.

Thus, it is an object of the present invention to make the treatment of microbial infections much more effective and efficient.

It is yet a further object of the present invention to provide treatment of microbial infections using laser energy transmitted via fiber optic laser delivery device.

It is yet a further object of the present invention to provide an improved method and apparatus for treatment of microbial infections of toenails, including onychomycosis.

DETAILED DESCRIPTION OF THE PREFERRED EMBODIMENT

Figure 1:
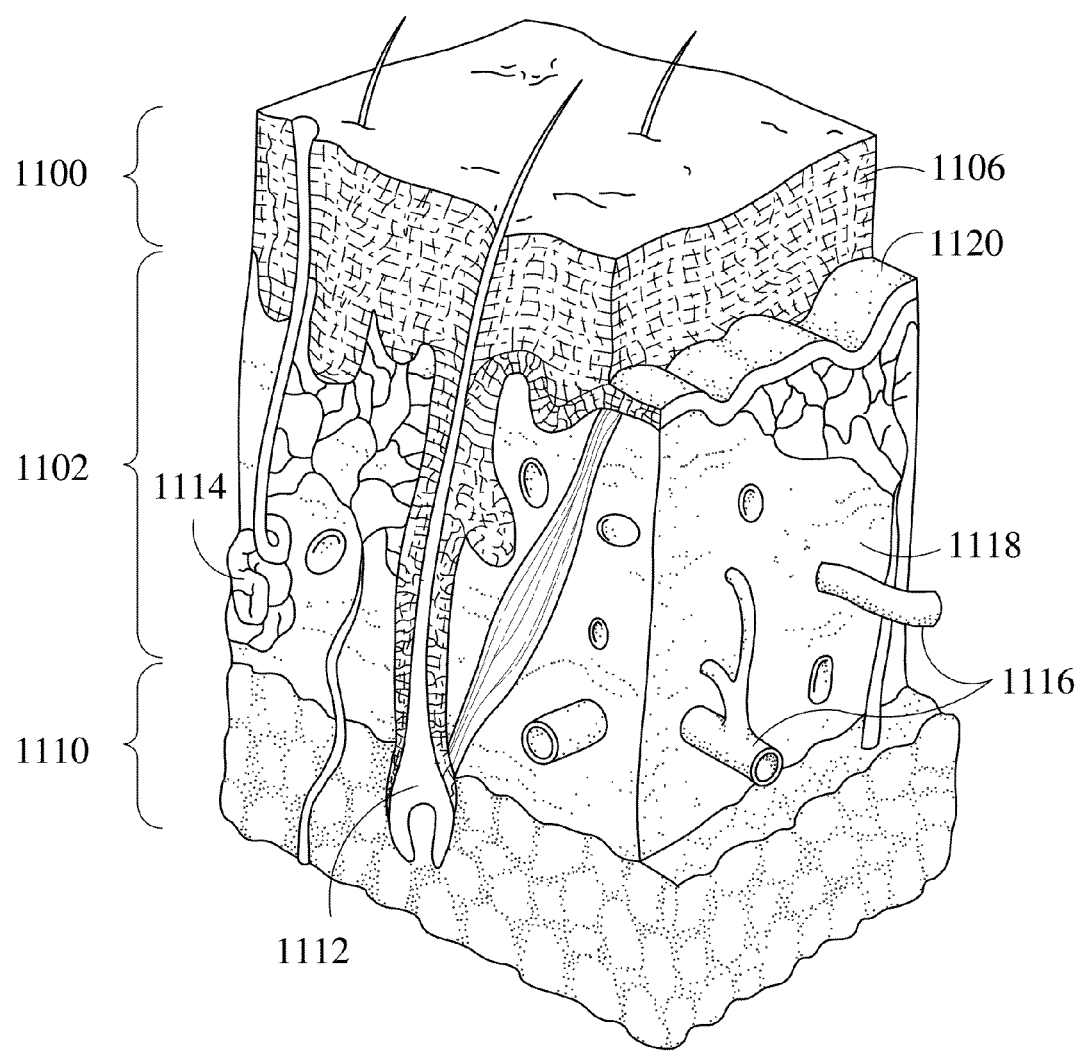
FIG. 1 is a cross-section view of typical skin tissue.

The description that follows is presented to enable one skilled in the art to make and use the present invention, and is provided in the context of a particular application and its requirements. Various modifications to the disclosed embodiments will be apparent to those skilled in the art, and the general principals discussed below may be applied to other embodiments and applications without departing from the scope and spirit of the invention. Therefore, the invention is not intended to be limited to the embodiments disclosed, but the invention is to be given the largest possible scope which is consistent with the principals and features described herein.

It will be understood that while numerous preferred embodiments of the present invention are presented herein, numerous of the individual elements and functional aspects of the embodiments are similar. Therefore, it will be understood that structural elements of the numerous apparatus disclosed herein having similar or identical function may have like reference numerals associated therewith.

Definitions

An "absorption coefficient" of a substance is a measure of the fraction of incident light that is absorbed when light is passed through the substance. The absorption coefficient (typically in units of $cm^{-1}$) varies with the nature of the absorbing substance and with the wavelength of the light.

"Collagen" as used herein refers to any of the several types of collagen.

"Monochromatic" light is of one wavelength or a narrow range of wavelengths. If the wavelength is in the visible range, monochromatic light will be of a single color. As used herein, "monochromatic" refers to light that has a bandwidth of less than about 100 nm. More preferably, the bandwidth will be less than about 10 nm, and most preferably less than about 1 nm.

"Non-coherent light energy" is light that is non-laser. Unlike laser light, which is characterized by having its photon wave motions in phase, the wave motions of the photons that make up non-coherent light are in a randomly occurring phase order or are otherwise out of phase.

A "wound" as used herein, refers to any damage to any tissue in a living organism. The tissue may be an internal tissue, such as the stomach lining or a bone, or an external tissue, such as the skin As such, a wound may include, but is not limited to, a gastrointestinal tract ulcer, a broken bone, a neoplasia, and cut or abraded skin A wound may be in a soft tissue, such as the spleen, or in a hard tissue, such as bone. The wound may have been caused by any agent, including traumatic injury, infection or surgical intervention.

FIG. 1 is a cross-section view of typical skin tissue. The uppermost layer 98 of typical skin tissue is composed of dead cells which form a tough, horny protective coating. A thin outer layer, the epidermis 1100 and a thicker inner layer, the dermis 1102. Intertwining S-like finger shaped portions are at the interface between the epidermal papillary layer 1106 and the dermal papillary layer, and extend downward. Beneath the dermis is the subcutaneous tissue 1110, which often contains a significant amount of fat. It is the dermis layer which contains the major part of the connective collagen which is to be shrunk, in a preferred embodiment at an approximate target depth of between about 100 and 300 microns, according to the method of the present invention, though viable collagen connective tissue also exists to a certain degree in the lower subcutaneous layer as well. Other structures found in typical skin include hair and an associated follicle 1112, sweat or sebaceous glands and associated pores 1114, blood vessels 1116 and nerves 1118. Additionally, a pigment layer 1120 might be present. It will be understood that the drawing is representative of typical skin and that the collagen matrix will take different forms in different parts of the body. For example, in the eyelids and cheeks the dermis and subcutaneous layers are significantly thinner with less fat than in other areas. The target depth will be a function of the amount of scattering in the particular skin type and the associated absorption coefficient of the tissue. Furthermore, in some cases the actual target depth will correspond to one half the thickness of the subject tissue. For example, the target depth of tissue ½ inch thick might be about ¼ inch below the surface of the skin.

A. Damage to Tissue

Optimum Wavelength: 1.3-1.4 Microns

Methods and devices for modulating collagen biosynthesis are provided. The methods involve focusing non-coherent light energy of a predetermined wavelength to a target site where collagen biosynthesis can potentially occur. Depending upon the particular wavelength employed, collagen biosynthesis is either inhibited or stimulated. Generally, wavelengths in the red and near-infrared portion of the electromagnetic spectrum stimulate collagen biosynthesis, while longer wavelengths inhibit collagen biosynthesis.

The optimal wavelength within these ranges is influenced by whether the light energy must pass through overlying tissue before reaching the target site. In such cases where the target site is shielded by other tissue, the light energy is transmitted through the shielding tissue and focused on the target site so that the desired energy level is obtained at the target site. Because transmission of light through tissue is highly wavelength specific, one should choose a wavelength that is not highly absorbed by overlying tissue.

To achieve the desired energy density, the light energy is delivered to the target site for a sufficient time period. The time period necessary depends on the energy flux delivered to the target site by the light delivery apparatus. The light can be delivered as a single pulse or as a multiplicity of pulses. Often, the use of short pulses is preferred, as the shorter pulses cause less undesirable heating of the tissues surrounding the target site than does a single pulse of longer duration. Preferably, a higher-power shorter-duration pulse is used, rather than a low-power long-duration pulse. Typical pulse durations are between about 0.01 and 1.0 seconds, most preferably about 0.1 seconds.

Light Delivery Apparatus

In a preferred embodiment, a monochromatic or nearly monochromatic light source is used. By choosing a light source that emits monochromatic or nearly monochromatic light, the need to filter or focus the light to the desired wavelength is eliminated. Several types of monochromatic or nearly monochromatic light source are known to those of skill in the art. See, e.g., LaRocca, supra., for types and sources of monochromatic light sources.

Light energy used in the claimed methods is preferably collimated, in addition to being of a predetermined wavelength or range of wavelengths. Collimation can be achieved by any of several methods known to those of skill in the art. For example, passing light through fiber optics of various core diameters will achieve collimation. Suitable fiber optic instrumentation is available from EG&G Opto-Electronics of Salem, Mass. Optical fibers are described, for example, in Brown, T. G., "Optical Fibers and Fiber-Optic Communications," In Handbook of Optics, Vol. U, Ch. 10, Bass, M., ed., McGraw-Hill, New York, pp. 10.1 et seq.

The light energy is focused to the target site as a spot having a diameter that is appropriate for the particular treatment being undertaken. Where inhibition of collagen biosynthesis in a relatively small area is used, the light is focused to a correspondingly small spot at the target site. Typically, the light energy is focused to a spot with a diameter in the range of about 0.25 to about 2.0 millimeters. The focusing step also concentrates the light to an energy flux that is sufficient to achieve the desired inhibition when delivered to the target site for an appropriate period of time.

Methods for focusing light to achieve a desired energy flux and spot diameter are known to those of skill in the art. For example, a focusing lens made of glass, silica, or refractory material such as diamond or sapphire is commonly employed. In a preferred embodiment, the focusing lens directs the non-coherent light energy to an optical fiber of an appropriate core diameter and composition. For example, a 100 µm diameter low-OH silica optic fiber is appropriate. A fiber that produces a relatively low amount of transmission loss is preferred, preferably less than about 15% loss over a length of up to ten meters. The fiber is typically mounted in a shaft for delivery of the non-coherent light energy to the tissue. The output end of the shaft is preferably fitted with an output tip that can dir maintaining the delivery end of the fiber a desired distance away from the tissue. This distance can be varied by substituting a longer or shorter output tip, or by slidably adjusting the position of the output tip on the shaft.

For some applications, it is desirable to use an output tip that directs the noncoherent focused light out of its side, rather than through the end of the fiber. Means for accomplishing this are known to those of skill in the art. For example, U.S. Pat. No. 5,129,895 describes the use of a reflecting surface at the end of the fiber combined with lens action on the fiber side.

Therapeutic Applications

To enhance wound healing, collimated fight energy of an appropriate wavelength is delivered to the wound at an energy density sufficient to stimulate collagen biosynthesis. Ile light energy can be delivered as a single pulse, or more preferably, as a series of short pulses. The use of short pulses reduces the likelihood of undesired heating of the tissue. Preferably, the light energy delivered is sufficient to stimulate collagen biosynthesis, but is insufficient to inhibit cell proliferation.

Figure 2:
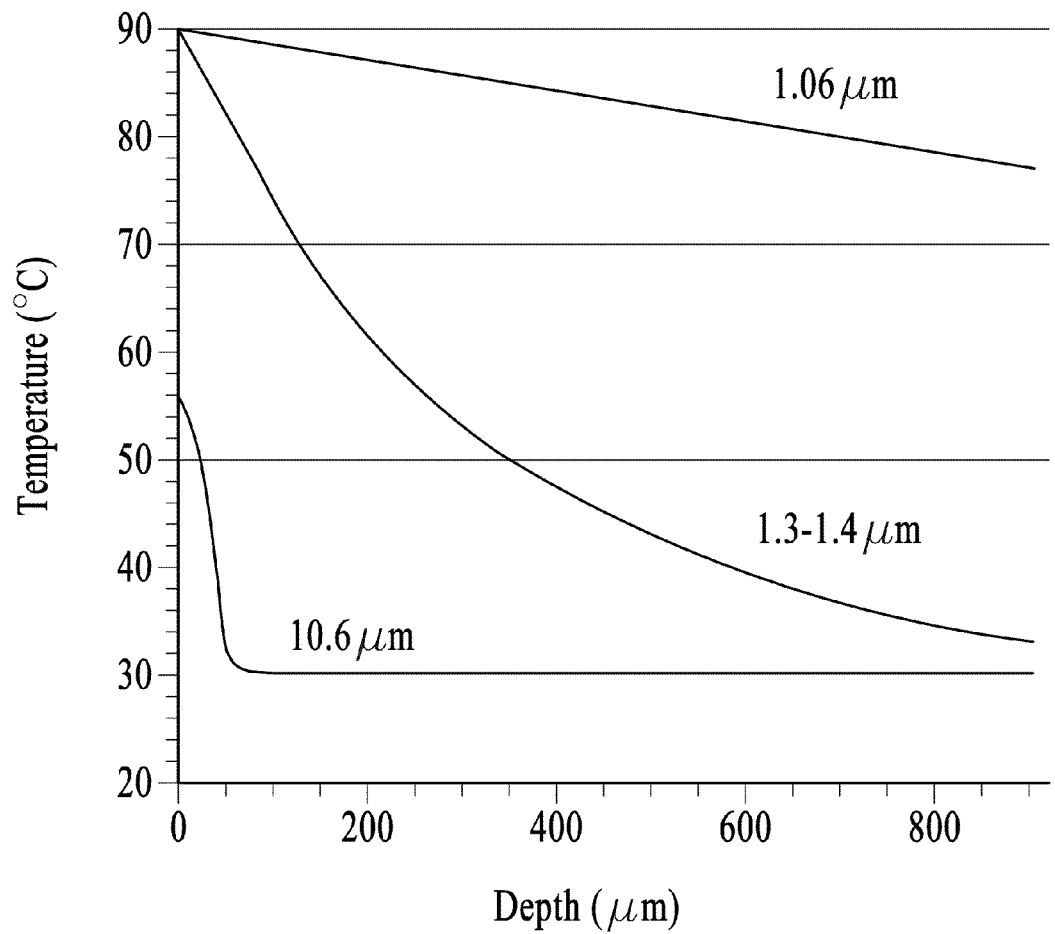
FIG. 2 is a graph demonstrating the temperature gradient through a portion of the skin as a function of both the wavelength of incident laser energy and the depth of laser radiation penetration.
Figure 3:
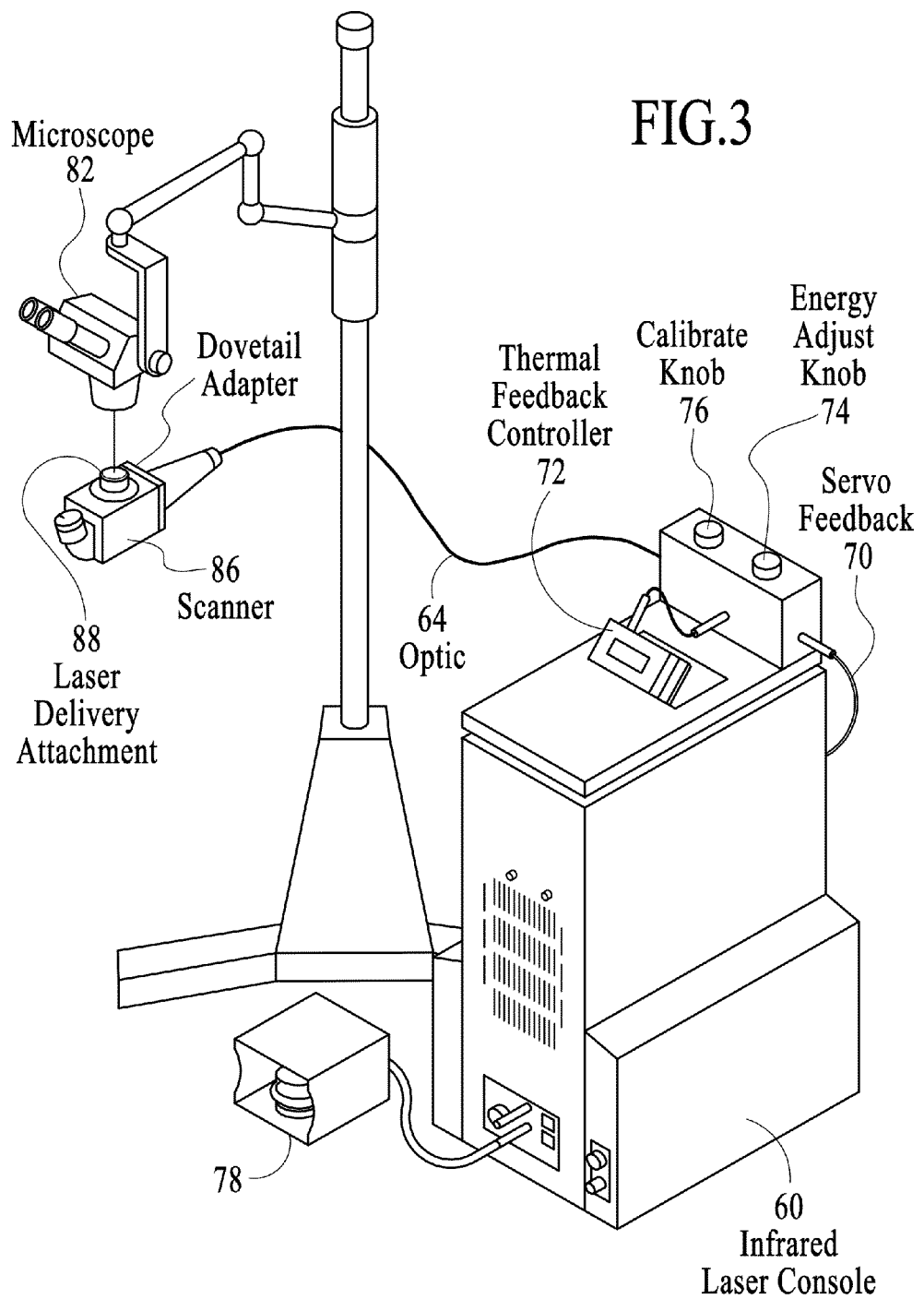
FIG. 3 is a schematic view of a microscope mounted scanner for a temperature controlled collagen shrinkage device used in the present invention.

FIG. 2 is a graph demonstrating the temperature gradient through a portion of the skin as a function of both the wavelength of incident laser energy and the depth of laser radiation penetration. No external cooling is used. The graph demonstrates a change in temperature ($\Delta T$) of about 60° C. and all curves are shown for the time point 1 millisecond following exposure to the laser energy. The graph shows three lines corresponding to laser wavelengths of 10.6 microns, 1.3-1.4 microns and 1.06 microns.

The present invention utilizes laser energy having a wavelength between about 1 and about 12 microns, more preferably between about 1.2 and about 1.8 microns, and more preferably about 1.3-1.4 microns. This type of laser energy is most frequently produced by a Nd:YAG, Nd:YAP or Nd:YALO-type laser. A laser operating at these wavelengths may either have a high repetition pulse rate or operate in a continuous wave mode. This laser has been investigated in the medical community as a general surgical and tissue welding device, but has not been used for collagen tissue shrinkage in the past. Indeed, the prior art teaches away from the use of laser energy at 1.3-1.4 microns for shrinking human collagen.

The Nd:YAG, Nd:YAP and Nd:YALO-type lasers are sources of coherent energy. This wavelength of 1.3-1.4 microns is absorbed relatively well by water, and as a result is attractive for tissue interaction. It is also easily transmitted through a fiber optic delivery system as opposed to the rigid articulated arm required for the $CO_2$ laser. Very precise methods of controlling laser systems and optically filtering produced light currently exist. By selecting the appropriate combination of resonance optics and/or anti-reflection coatings, wavelengths in the range of 1.3-1.4 microns and even 1.32-1.34 microns can be produced.

Figure 6:
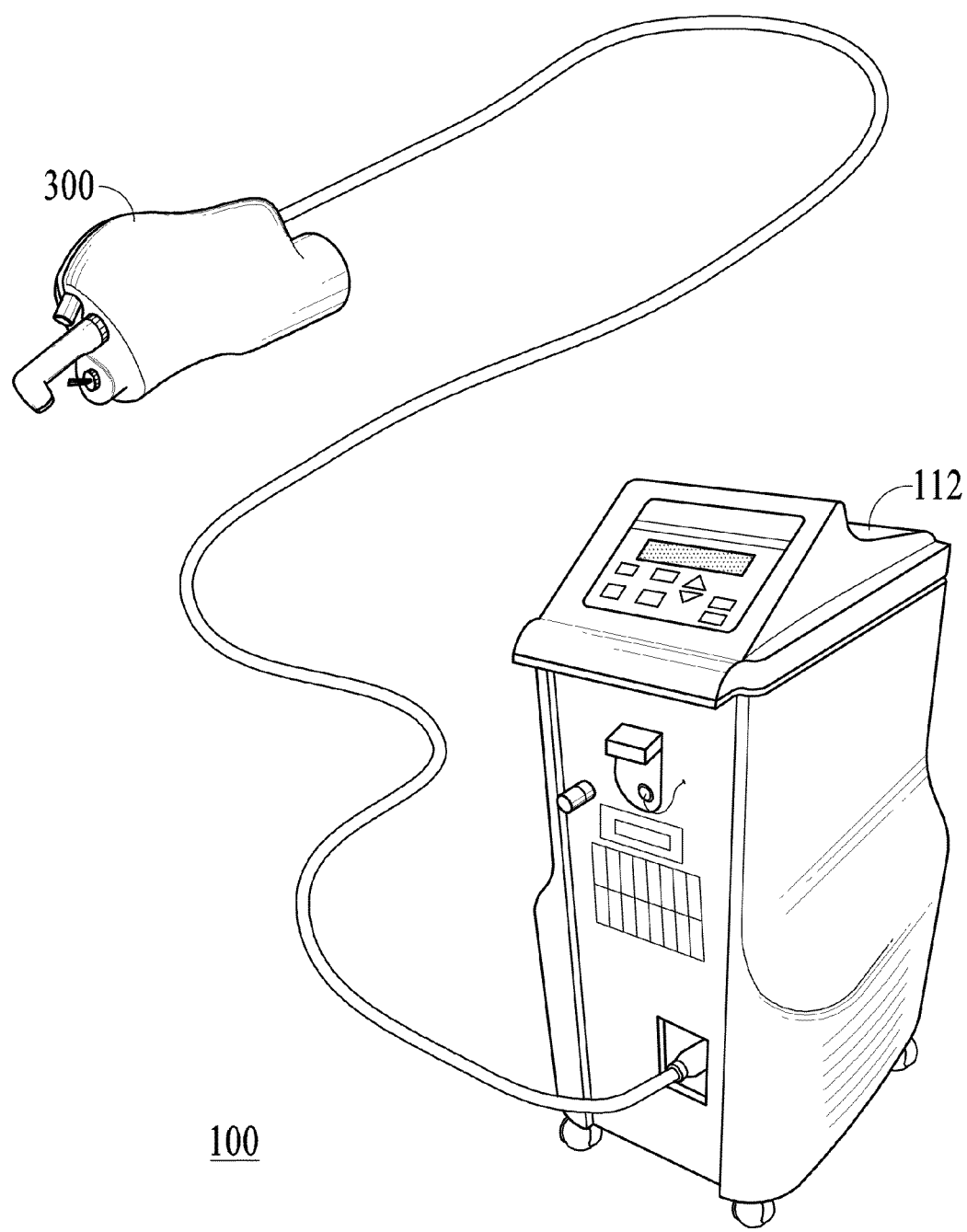
FIG. 6 is a representative illustration showing an embodiment of laser control system with cooling spray device devices and methods of the present invention 100.

FIG. 6 is a schematic view of a microscope mounted scanner for a temperature controlled collagen shrinkage device used in the present invention. In this view, a laser console 60 is installed adjacent a floor-mounted microscope 62. A fiber optic cable 64 conducts laser energy from the laser source to the scanner 66. A laser delivery attachment 68 may be necessary to conduct the laser energy in an appropriate beam pattern and focus. In this embodiment of the invention, servo feedback 70 signals are also conducted along the fiber optic back to the laser console. The servo feedback signals could also be directed back to the laser console via an additional fiber optic or other wiring or cabling. This servo feedback may comprise thermal or optical data obtained via external sensors or via internal systems, such as a fiber-tip protection system which attenuates the laser energy transmitted, to provide control in operation and to prevent thermal runaway in the laser delivery device. Thus, a thermal feedback controller 72 will regulate the laser energy being transmitted. This controller can comprise an analog or digital PI, PD or PID-type controller, a microprocessor and set of operating instructions, or any other controller known to those skilled in the art. Other preferred embodiments can also be provided with additional features. For example, the surgeon or technician operating the laser could also manipulate an energy adjust knob 74, a calibration knob 76 and a footpedal 78. Thus, in a preferred embodiment, a very accurately adjustable system is provided which allows a surgeon to deliver laser energy via a computer controlled scanning device, according to instructions given by the surgeon or an observer inspecting the region of the skin to be treated through a very accurate microscope. Once a region to be treated is located, the scanner can deliver a very precise, predetermined amount of laser energy, in precisely chosen, predetermined regions of the skin over specific, predetermined periods of time.

In a preferred embodiment, the invention utilizes 1200-2000 nm wavelength. As an example, an Nd:YAG laser at 1320 nm wavelength, [such as the CoolTouch™ 130, CoolTouch Corp., Roseville, Calif.] can be the source of treatment energy. At 1320 nm the absorption depth in tissue is such that energy is deposited throughout the upper dermis, with most absorption in the epidermis and upper dermis, a region including the top 200 to 400 microns of tissue. The energy falls off approximately exponentially with the highest level of absorbed energy in the epidermis. Optical heating of skin follows exposure to the laser energy. If the time of exposure to the laser is very short compared to the time required for heat to diffuse out of the area exposed, the thermal relaxation time, than the temperature rise at any depth in the exposed tissue will be proportional to the energy absorbed at that depth. However, if the pulse width is comparable or longer to the thermal relaxation time of the exposed tissue than profile of temperature rise will not be as steep. Conduction of thermal energy occurs at a rate proportional to the temperature gradient in the exposed tissue. Lengthening the exposure time will reduce the maximum temperature rise in exposed tissue.

For example at 1.3 microns the laser pulse width may be set to 30 milliseconds and fluence to less than 30 joules per square centimeter. This prevents excessive heat build up in the epidermis, which is approximately the top 100 microns in skin. The papillary dermis can then be heated to a therapeutic level without damage to the epidermis. The epidermis will reach a temperature higher than but close to that of the papillary dermis.

The epidermis is more resilient in handling extremes of temperature than most other tissue in the human body. It is therefore possible to treat the papillary dermis in conjunction with the epidermis without scarring or blistering, by treating both layers with laser energy and allowing a long enough exposure time such that the thermal gradient between the epidermis and underlying layers remains low. In this way the underlying layers can be treated without thermal damage to the epidermis.

A wavelength of 1.3 microns is used in this embodiment to treat the middle layers of skin Other wavelengths such as 1.45 or 2.1 microns may by used to treat more superficial layers of skin by this method. Visible light lasers, intense pulsed light sources, energy delivery devices such as electrical generators, ultrasonic transducers, and microdermabrasion devices may also be used to initiate a wound healing response without significant surface wounding. The use of growth factors in conjunction with these devices allows for more superficial treatments and improved response.

In one embodiment the invention utilizes an Nd:YAG laser at 1320 nm wavelength, [such as the CoolTouch™ 130, CoolTouch Corp., Roseville Calif.] can be the source of treatment energy. At 1320 nm the absorption depth in tissue is such that energy is deposited throughout the upper dermis, with most absorption in the epidermis and upper dermis, a region including the top 200 to 400 microns of tissue. The energy falls off approximately exponentially with the highest level of absorbed energy in the epidermis. Optical heating of skin follows exposure to the laser energy. If the time of exposure to the laser is very short compared to the time required for heat to diffuse out of the area exposed, the thermal relaxation time, than the temperature rise at any depth in the exposed tissue will be proportional to the energy absorbed at that depth. However, if the pulse width is comparable or longer to the thermal relaxation time of the exposed tissue than profile of temperature rise will not be as steep. Conduction of thermal energy occurs at a rate proportional to the temperature gradient in the exposed tissue. Lengthening the exposure time will reduce the maximum temperature rise in exposed tissue.

The present invention also incorporates herein by specific reference, in their entireties, the following issued U.S. patents:

U.S. Pat. No. 5,885,274 issued Mar. 3, 1999 titled FLASH LAMP FOR DERMATOLOGICAL TREATMENT, U.S. Pat. No. 5,968,034 issued Oct. 19, 1999 titled PULSED FILAMENT LAMP FOR DERMATOLOGICAL TREATMENT, U.S. Pat. No. 5,820,626 issued Oct. 13, 1998 titled COOLING LASER HANDPIECE WITH REFILLABLE COOLANT RESERVOIR, U.S. Pat. No. 5,976,123 issued Nov. 2, 1999 titled HEART STABILIZATION, U.S. Pat. No. 6,273,885 issued Aug. 14, 2001 titled HANDHELD PHOTOEPILATION DEVICE AND METHOD.

The present invention also incorporates herein by specific reference, in their entireties, the following pending U.S. patent applications: application Ser. No. 09/185,490 filed Nov. 3, 1998 titled SUBSURFACE HEATING OF TISSUE, application Ser. No. 09/364,275 filed Jul. 29, 1999 titled THERMAL QUENCHING OF TISSUE.

Figure 4:
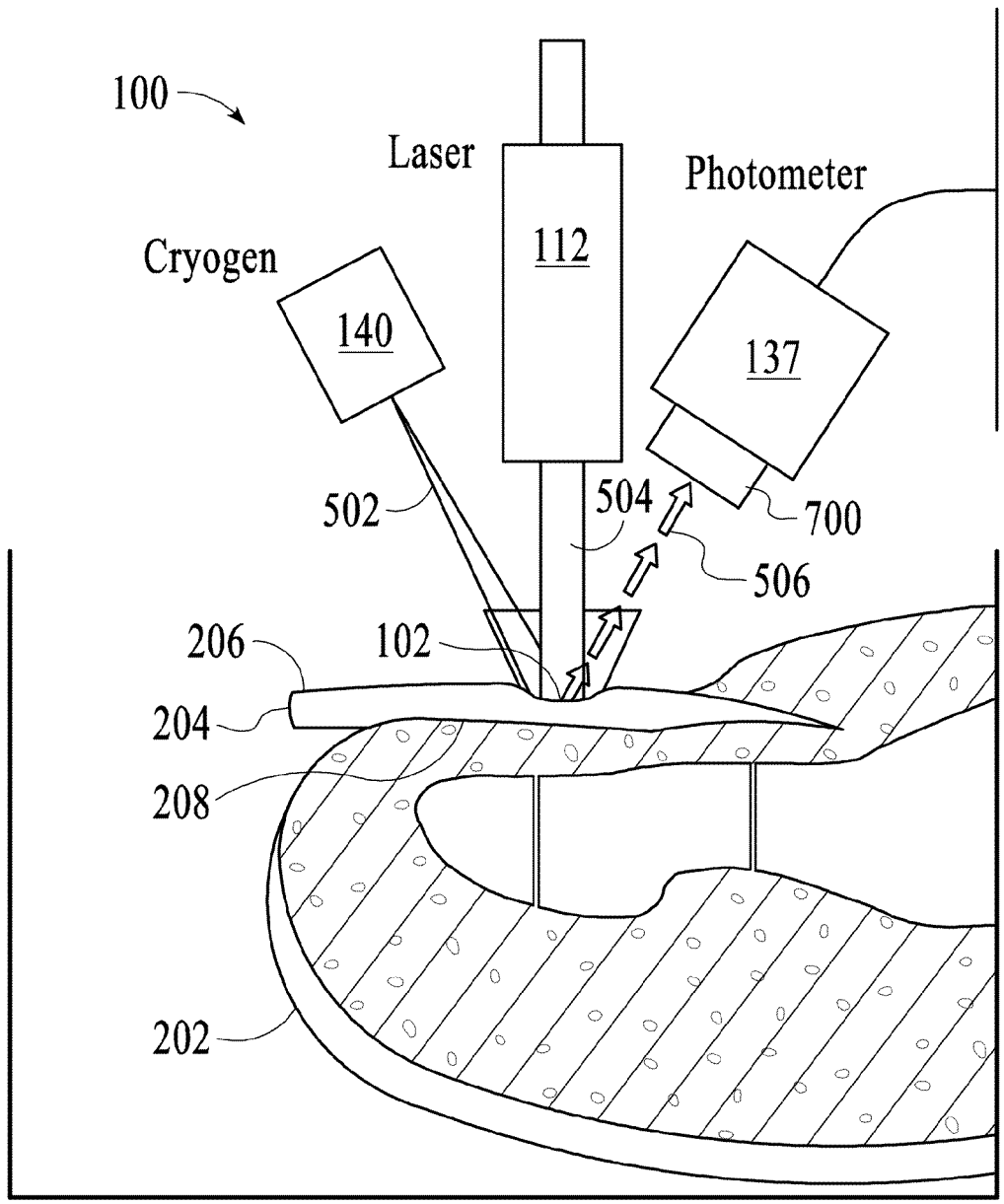
FIG. 4 is a representative illustration showing an embodiment of the apparatus and method of treatment of microbial infections using hot and cold thermal shock and pressure 100 of the present invention.

FIG. 4 is a representative illustration showing an embodiment of the apparatus and method of treatment of microbial infections using hot and cold thermal shock and pressure 100 of the present invention.

The present invention uses an automatic target thermal feedback to precisely control the dosimetry of the laser 112, or intense light or intense pulsed light IPL irradiation, to prevent damage to surrounding tissue and reduce pain. A non-contact thermal detector 137, such as made by Raytek or equivalent, is built into a handpiece along with a lens to focus the laser delivery fiber optic 504 or a laser diode. The output of the non-contact thermal detector 137 is used to adjust the power output of the laser 112 to maintain a selected treatment temperature at the treatment site 102.

A preferred embodiment of the present invention utilizes a 1320 nm continuous or pulsed laser 112 that is capable of delivering 2 to 5 watts of energy, or more or less, with continuous or pulsed cryogen cooling 140. The energy is delivered from a handpiece that focuses the light into a 2-10 mm diameter spot on the treatment tissue, treatment site 102. A non contact thermal sensor 137 detects the temperature of the treated spot and send a signal to the laser 112 control system which then adjusts the energy to maintain a pre selected target temperature at the spot. A continuous or pulsed cooling spray device 140 is incorporated into the handpiece to deliver a spray of coolant 502 to the target treatment spot 102 after each laser treatment interval.

It will be understood that the site of infection is associated with the nail 204 of the finger or toe 202 the nail has a plate 206 as well as a bed 208.

Figure 5:
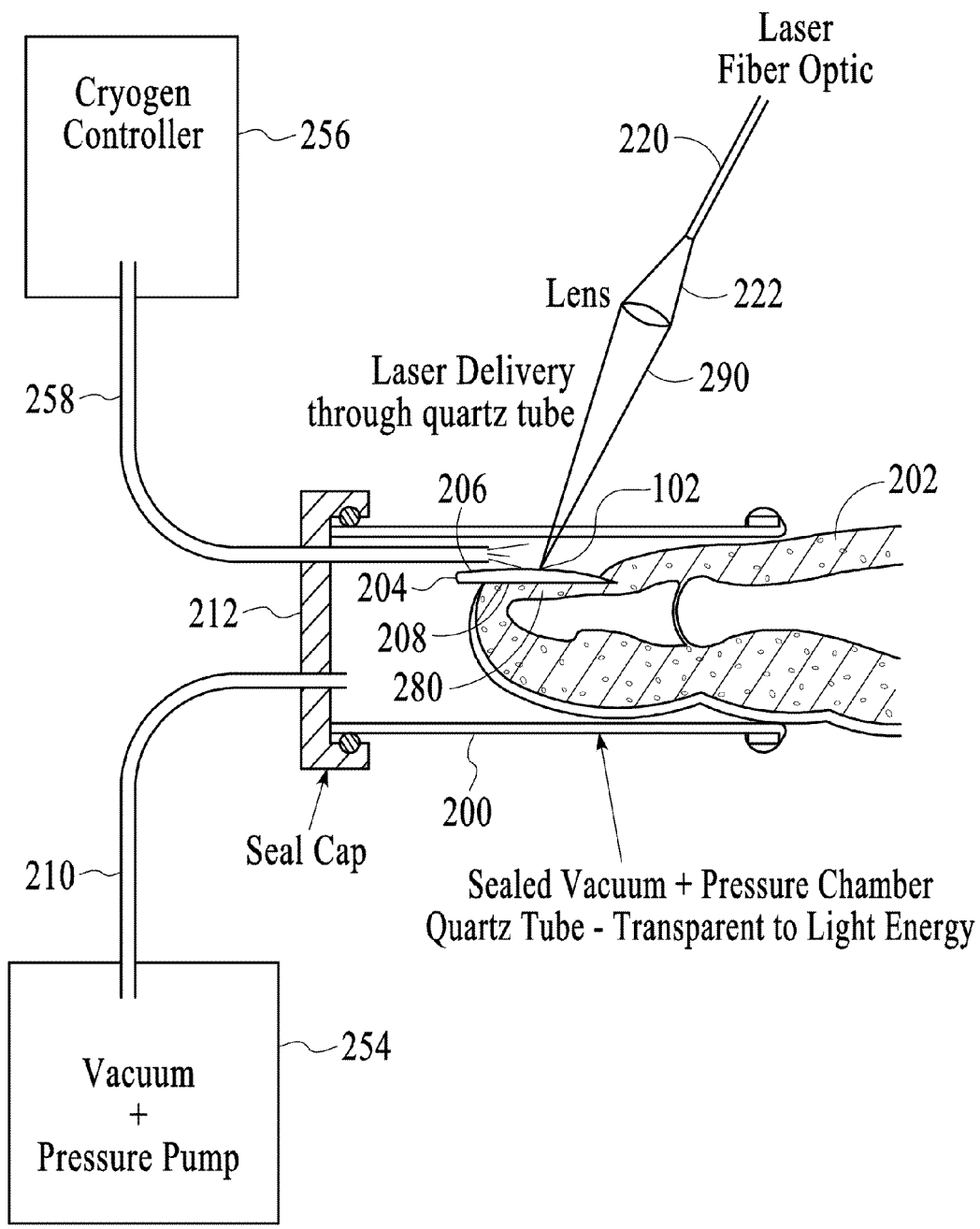
FIG. 5 is a representative illustration showing an embodiment of a transparent toe jacket 200 of the present invention 100.

FIG. 5 is a representative illustration showing an embodiment of a transparent toe jacket 200 of the present invention 100.

As described above, the present invention uses localized and temporary external vacuum pressure through the use of a transparent toe jacket 200. In one embodiment, jacket 200 is a quartz tube that is transparent to light energy, seals vacuum and acts as a pressure chamber. This jacket 200 seals around the finger or toe 202 and is instrumented with a vacuum or pressure pump 254 to lower or increase the atmospheric pressure around it, optionally including the toenail-fungus-toe space, prior to treatment. In an embodiment of the present invention, cryogenic cooling controller 256 provides such coolant via cooling supply lines 258. Cooling lines 258 and vacuum lines 210 lead through sealing cap 212 or other portion of the toe jacket 200. The toe jacket 200 provides a unique, sealed vacuum and pressure chamber made of quartz tube transparent to light energy. Laser energy can be directed to impinge directly onto the nail plate 206. It will be understood that energy not absorbed by the nail plate 206 itself will pass therethrough to the nail bed 208 and into the underlying tissue 280 of the finger or toe being treated. Preferential absorption of laser energy 290 having a wavelength 1470 nm by the nail plate 206 of the infected toe or finger nail 204 results in a controlled elevation in temperature to a temperature effective at disinfection of the infected regions or areas without causing irreversible thermal damage to the infected nails.

Fiber optic laser delivery system 220 comprises optical fibers as well as lens mechanism 222, and optional filters, convertors or other beam modifiers which can be coupled to the toe jacket 200 as desired. In an embodiment, laser energy 290 is delivered through fiber optic or other quartz tube structure 220.

In an embodiment, the present invention is a method for treatment of microbial infection of human skin The method consists of the following steps: 1. Treating a subsurface layer of infected skin with a source of electromagnetic energy sufficient to cause stimulation of an immune response without thermal damage to the epidermis; and 2. Using a vacuum attachment over the infection site to reduce the pressure around the infected site and thereby to reduce the effective boiling temperature of water located in the surrounding tissue, thereby improving treatment efficiency and/or reducing associated patient pain. The method can further include the step of applying an anti-microbial agent directly to the upper surface of the dermis, thereby improving treatment efficiency. More specifically, the method can used when the microbial infection is a viral infection. More specifically, the method can be used when the viral infection is a wart.

FIG. 6 is a representative illustration showing an embodiment of laser control system with cooling spray device devices and methods of the present invention 100. As described above, a preferred embodiment of the present invention utilizes a 1320 nm continuous or pulsed laser 112 that is capable of delivering 2 to 5 watts of energy, with continuous or pulsed cryogen cooling. The energy is delivered from a handpiece 300 that focuses the light into a 2-10 mm diameter spot on the target treatment spot 102. The laser 112 control system adjusts the energy to maintain a pre selected target temperature at the spot. A continuous or pulsed cooling spray device is incorporated into the handpiece 300 to deliver a spray of coolant to the target treatment spot 102 after each laser treatment interval.

The laser and coolant delivery handpiece 300 can be the CoolTouch® TQ10 model handpiece or equivalent. In an embodiment, the handpiece 300 can deliver laser energy 290 at a wavelength of 1320 nanometers at a fluence rate of 24 Joules per square centimeter. The handpiece 300 with integrated continuous or pulsed cryogen cooling reduces the surface temperature for nail protection allowing the laser energy 290 to be effectively targeted. Cooling can be provided adjustably pre, mid and post cooling to maximize patient comfort, safety and efficacy.

Treatment Agents

It will be understood that THE PRESENT INVENTION consists of applying liquid or gas directly to the target, i.e., to the infected nail. Furthermore, the liquid or gas may contain one of more of the following: pain reducing agent, antifungal agent, anti-microbial agent, antiseptic agent or disinfectant agent. It will be understood that there are a wide range of agents which are associated with pain reduction, anti-irritant, antifungal treatment, antimicrobial and antibiotic activity as well as antiseptic and disinfecting properties, the use of which is expressly contemplated herein.

Antifungal agents may include any antifungal agents useful in dermatological compositions. Examples of antifungal agents include, without limitation, Tea Tree oil and other naturally occurring oils and compounds, nystatin, ciclopirox and ciclopirox olamine, griseofulvin, itraconazole, fluconazole, ketoconazole, terbinafine, econazole, benzyl alcohol, undecylenic acid and salts thereof, benzyl benzoate and combinations thereof. Antifungal agents are well known in the art. One of ordinary skill in the art would understand, appreciate and recognize agents that are considered to be antifungal agents.

Antimicrobial agents may include any antimicrobial agents useful in dermatological compositions. Antimicrobial agents include, without limitation, benzoyl peroxide, povidone iodine, hexachlorphene, chlorhexidine, mupirocin, gentimycin, neomycin, bacitracin, polymixin, erythromycin, clindamycin, metronidazole, clarithromycin, silver sulfadiazine, dapsone, zinc pyrithione, cephalosporin, thymol, mafenide acetate, nitrofurazone, generators of nitric oxide benzyl alcohol, sulfamethoxazole, sulfasalazine, sulfasoxazole, acetylsulfasoxazole and combinations thereof. Antimicrobial agents are well known in the art. One of ordinary skill in the art would understand, appreciate and recognize agents that are considered to be antimicrobial agents.

Anti-irritants are well known in the art. One of ordinary skill in the art would understand, appreciate and recognize agents that are considered to be anti-irritants. Preferred anti-irritants include but are not limited to aloe vera gel, alpha bisabolol, allantoin, sorbitol, urea, lactic acid and salts, glucose derivatives, zinc acetate, zinc carbonate, zinc oxide, potassium gluconate, dimethicone, glycerin, petrolatum, lanolin, peramides, uric acid and salts, N-acetyl cysteine, and hydrocortisone.

Disinfectants are also well known in the art. One of ordinary skill in the art would understand, appreciate and recognize agents that are considered to be disinfectants. Preferred disinfectants include but are not limited to chlorine bleach or sodium hypochlorite Method of Treatment The following is taken from the CoolBreeze® (trademark) treatment guidelines for onychomycosis.

Patient Preparation:
1. Remove all lotions and skin care products, making certain that the skin of the foot and nail bed are completely dry prior to treatment.
2. Debridement of thickened nails might be necessary prior to laser treatment
3. Topical anesthetics are not recommended for the CoolBreeze mode. Anesthetics can interfere with the patient's ability to assess their comfort level.

Setting Treatment Parameters:

Fluence: Set at 5 Joules-Sec/cm2 (Range is 5-12 Joules-Seconds/cm2)

Adjust as needed to achieve a comfortable treatment for the patient.

When using higher fluences, the nail bed will reach target temperature more quickly and the speed of hand piece movement will need to be faster.

Target Temperature: Set at 39° C. (Range is 30°-42° C.)

The system will sound an audible alert, "Beep" when the target nail bed temperature is reached, as well as displaying the temperature on the control panel.

Each subsequent pass will increase temperature and the target temperature may be reached more quickly than anticipated.

Cryogen Cooling: Set at 40 msec (Range is 0-50 msec)

Cryogen will be delivered after the target temperature has been achieved.

NOTE: These guidelines are meant to establish starting parameters. In any given clinical procedure there are many variables involved, therefore the settings may need to be modified to accomplish the desired treatment goals.

The CoolBreeze® Mode

Micro-pulses of laser energy are delivered continuously when the foot pedal is depressed.

When the target nail bed temperature is reached, system will emit an audible high pitched, rapidly repeating, "beep". And the firing of the laser will slow.

Target temperature is displayed continuously on the display panel.

Movement of the Hand Piece

The speed of the hand piece movement and the selected fluence should allow the patient to experience mild to moderate warmth but not a sensation of hot or pain.

Target temperature and the confirming audible beep will be reached quicker with each additional pass and over areas of thin or debrided nails.

The skin of the toe should be stretched gently to flatten and move the skin surface away from the nail bed.

Lightly glide the gold footplate across the nail surface, avoiding treatment to the surrounding skin overlap by manipulating the hand piece in a smooth continuous motion.

Keep the hand piece perpendicular to the nail surface.

Each pass may be changed to a different orientation of movement for a more uniform distribution of energy.

Multiple passes will be needed before moving to the next toe.

Suggested Treatment Interval: Every Week for a Total of 3-4 Treatments

The number of the treatments is based on the condition of the nail and the amount of improvement desired.

Since toenails grow very slowly, the improvement is not seen immediately.

Changes in the nail bed are cellular in nature and take time. Improvement may be seen over a period of several months as the undamaged nail grows out.

Post Procedure Care:

Wear comfortable shoes and hosiery that allow your feet some breathing space.

Wear shoes, sandals or flip-flops in community showers or locker rooms.

Wash your feet every day, dry them thoroughly and use a good quality foot powder. Ask your doctor to recommend a foot powder with the right blend of ingredients.

Wear clean socks or stockings every day.

Keep toenails trimmed.

Disinfect pedicure tools before and after you use them. Note: Be sure to wipe the footplate with an appropriate disinfectant when finish treating each patient and before storing the handpiece.

The present invention is a method for treatment of warts on human skin. The method comprises treating a subsurface layer of virus infected skin with a source of electromagnetic energy sufficient to cause stimulation of an immune response without thermal damage to the epidermis, in conjunction with applying an anti-microbial agent directly to the upper surface of the dermis, thereby improving treatment efficiency, particularly where the infection is a viral infection such as a wart.

EXPERIMENTAL RESULTS

Experiment I

Soaking the nail in a water bath or with a wet towel laid on the toes increases the hydration of the nail and improves the absorption of 1320-2100 nm laser exposure. This allows effective treatments at lower power and reduces possible injury. Pre-treatment hydration will be described and discussed in later section of the application. Many prior art assumes that the treatment energy must be transmitted through the nail to treat the fungus itself in the nail bed.

Dry nail is composed of a fibrous protein called keratin. Experiment I tests showed that the use of a 1470 nm laser required very little power to heat up a nail that has been soaked in water to get hydrated. Equivalent heating of a dry nail requires 7 watts of 1064 nm, 2 watts of 1320 nm but only 1 watt of 1470 nm We discovered that there is an absorption peak in fibrous proteins at about 1500 nm that would explain this effect.

The present invention comprises the step of irradiating the microbe with infrared radiation using laser energy having a wavelength between about 1200 nm and about 2000 nm, and more particularly, using laser energy having a wavelength of about 1320 nm.

The present invention further comprises the step of irradiating the microbe with infrared radiation using laser energy having a wavelength between about 1450 nm and about 1550 nm, and more particularly, using laser energy having a wavelength of about 1470 nm.

Figure 7:
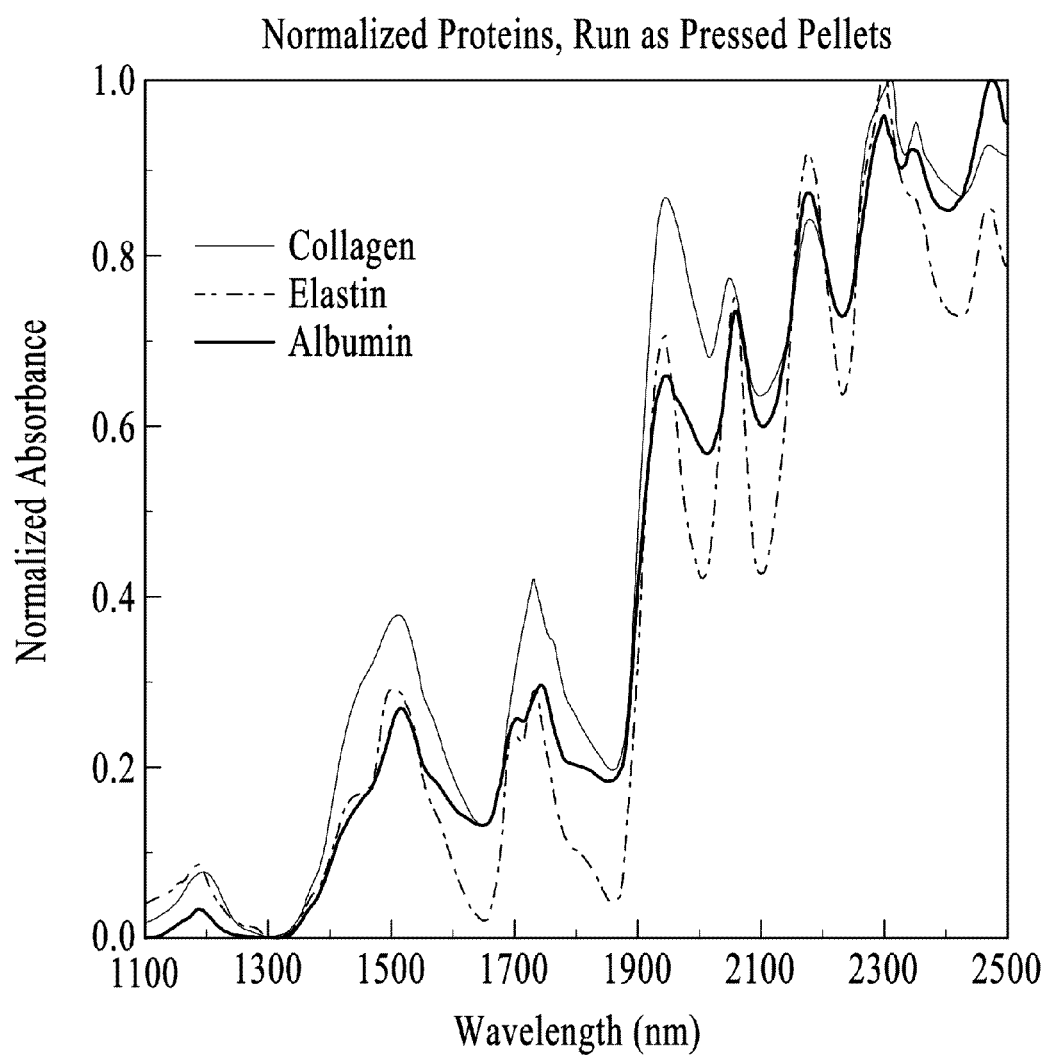
FIG. 7 is a representative chart showing an absorption curve that shows an absorption peak among similar proteins.
Figure 8:
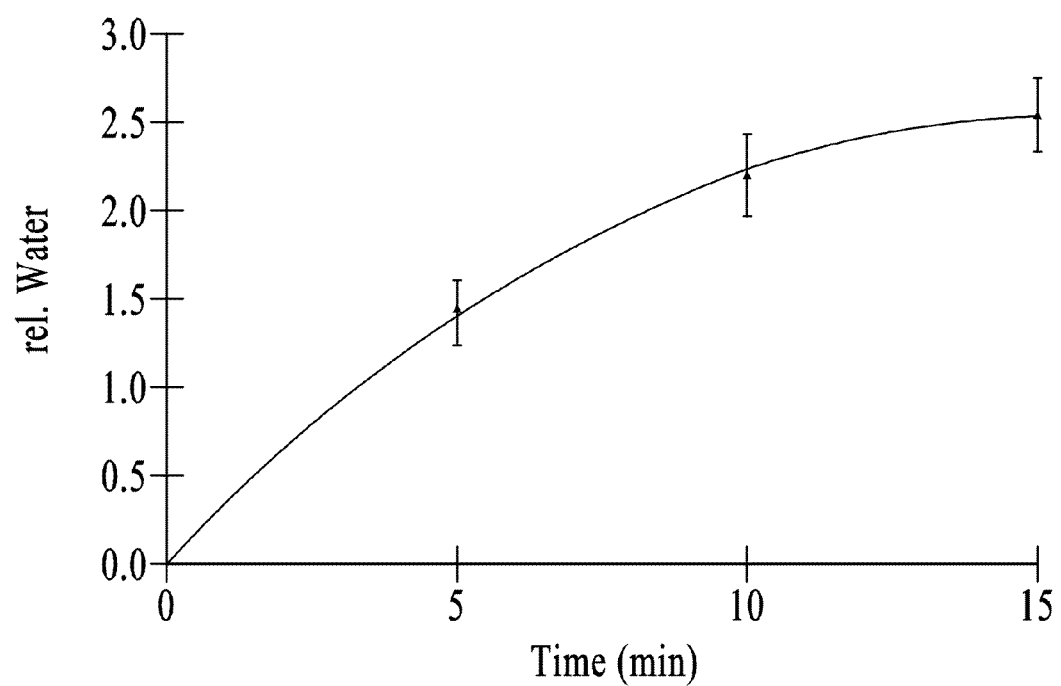
FIG. 8 is a representative chart showing time-dependent water uptake of toe nail samples [distal part].

FIG. 7 is a representative chart showing an absorption curve that shows an absorption peak among similar proteins. This is a significant new discovery and may lead to the treatment of onychomycosis with laser powers low enough to qualify for use by a non-physician and significantly lower the cost of the device.

Furthermore, there is an adverse event report to the FDA from a company that uses higher power 1064 nm lasers to treat toenails. There was blistering under the nail post operation. This is the kind of complication that can be avoided by using lower powered lasers that are more highly absorbed in the nail plate itself.

Experiment II

The CoolTouch® laser was used to treat infected large toenails in two individuals with a single treatment. New clear growth was seen at three months and the nails are completely clear at nine months post treatment. The laser was used on six Podiatry patients suffering from onychomycosis with a single treatment. At three months a band of clear nail is seen in all six patients and the site was tested and confirmed to be free of fungal infections.

Experiment III

In recent years, the eradication of Trichophyton rubrum (toenail fungus) has been attempted via laser irradiation. Researchers have recognized that this approach could result advantageous relative to oral, mechanical and chemical therapies. However, anticipating that the fluences required to achieve the necessary thermal effects on this fungus could unintentionally damage the underlying toe dermal layer, two auxiliary approaches are explored in this Experiment:
 (a) laser irradiation under vacuum pressure, with and without water dousing; and
 (b) rapid-cooling followed by laser heating (thermal shock).

The rationale behind these two approaches is that at low pressures, the temperature necessary to achieve fungus necrotic thermal effects, e.g., water evaporation/boiling, is significantly reduced, and thus requires lower fluences. Similarly, a thermal shock induced by a cryogen-cooled tip or spurt followed by laser irradiation may require much lower fluences to achieve the desired fungus necrosis. For all the tests in Experiment III as presented herein, CoolTouch™, model CT3™ plus, 1320 nm laser was used with 50 ms pulse duration and 20 Hz to irradiate fungi colonies grown on Petri dishes.

The vacuum pressure experiments, as in Experiment a, consisted of exposing fungi colonies to a sub-atmospheric pressure of 84.7 kPa or 25 in Hg with and without water dousing for 5 minutes, followed by laser irradiation with fluence of 4.0 J/cm$^2$ and total energies ranging from 40-90 J.

The thermal shock experiments, as in Experiment b, consisted of three separate sections:
 1. Control—Cooling the fungus to 0° C. at an approximate rate of 0.39° C./min and then irradiating to 45-60° C.;
 2. Slow Cooling the fungus to −20° C. at a rate of 1.075° C./min and irradiating to 45° C.; and
 3. Quick Cooling the fungus to −20° C. at a rate of 21.5° C./min and irradiating to 45° C.

All three types of thermal shock experiments were performed at a fluence of 4.8 J/cm$^2$. Thus far, fungus growth rate over an one week period was the only criterion used to assess the feasibility of each of these procedures. Our results indicate that both the vacuum (a) and thermal shock (b) approaches hamper the growth rate of fungi colonies relative to untreated control samples, especially the combination of water dousing or hydration prior to laser irradiation under vacuum conditions (a) and slow cooling rate preceding rapid laser irradiation for a thermal shock effect.

Figure 9:
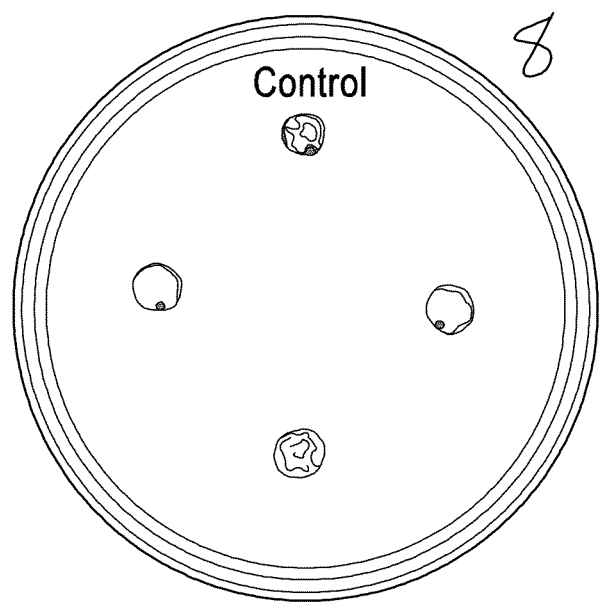
FIG. 9 is a representative illustration showing an example of plate set up with new samples of fungus.

Material and Method:

An isolate of *T. rubrum* was obtained from American Type Culture Collection (Manassas, Va.) and was cultivated on potato dextrose agar. Four-millimeter biopsy punch samples of the primary colonies were then transplanted to new plates containing pure potato dextrose agar as medium, four colonies per plate, and immediately subjected to the treatments described below. FIG. 9 is a representative illustration showing an example of plate set up with new samples of fungus. As shown in FIG. 9, a typical arrangement of the 4 fungi colonies on a Petri dish is illustrated. The number "8" refers to the experiment number for categorization purposes only. One colony of each plate was used for one of three types of controls: (1) completely untreated, (2) exposed to 84.7 kPa or 25 in Hg vacuum pressure, non-irradiated, (3) cooled to approximately 0° C., non-irradiated. All control samples were left to grow inside an incubator at 30° C. temperature with no $O_2$ or $CO_2$ control. Treated samples were also introduced into the incubator after the procedures and allowed to grow under the same conditions.

Figure 10:
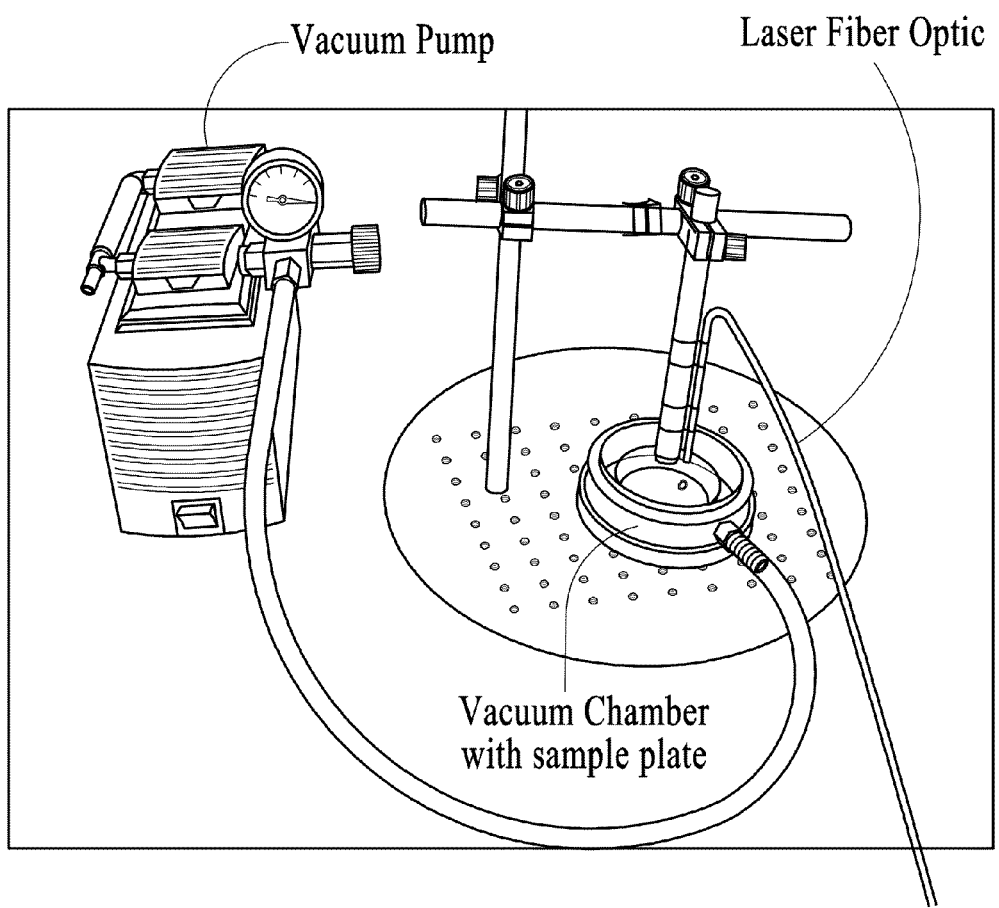
FIG. 10 is a representative illustration showing the set up for vacuum procedure.

The above-mentioned vacuum conditions (a) and thermal shock (b) procedures were as follows:

Vacuum Conditions Procedure:

FIG. 10 is a representative illustration showing the set up for vacuum conditions procedure. The vacuum-treated samples were divided into two subsets. Those denoted "V", were dry samples placed under −84.7 kPa or 25 in Hg pressure for approximately 5 minutes and subsequently exposed to laser irradiation, which was provided by a CoolTouch™ Q-switched, Nd:YAG laser, 1320 nm, 20 Hz, and 4 mm beam diameter, using a fluence of 4.0 J/cm$^2$ per pulse and an exposure time of 2-20 seconds. Those denoted "VW" followed the same procedure as "V" except that they were first heavily doused or hydrated in water before being exposed to vacuum pressure and laser irradiation. Vacuum control samples is only placed under −84.7 kPa or 25 in Hg pressure for approximately 5 minutes and not followed by laser irradiation.

Figure 11:
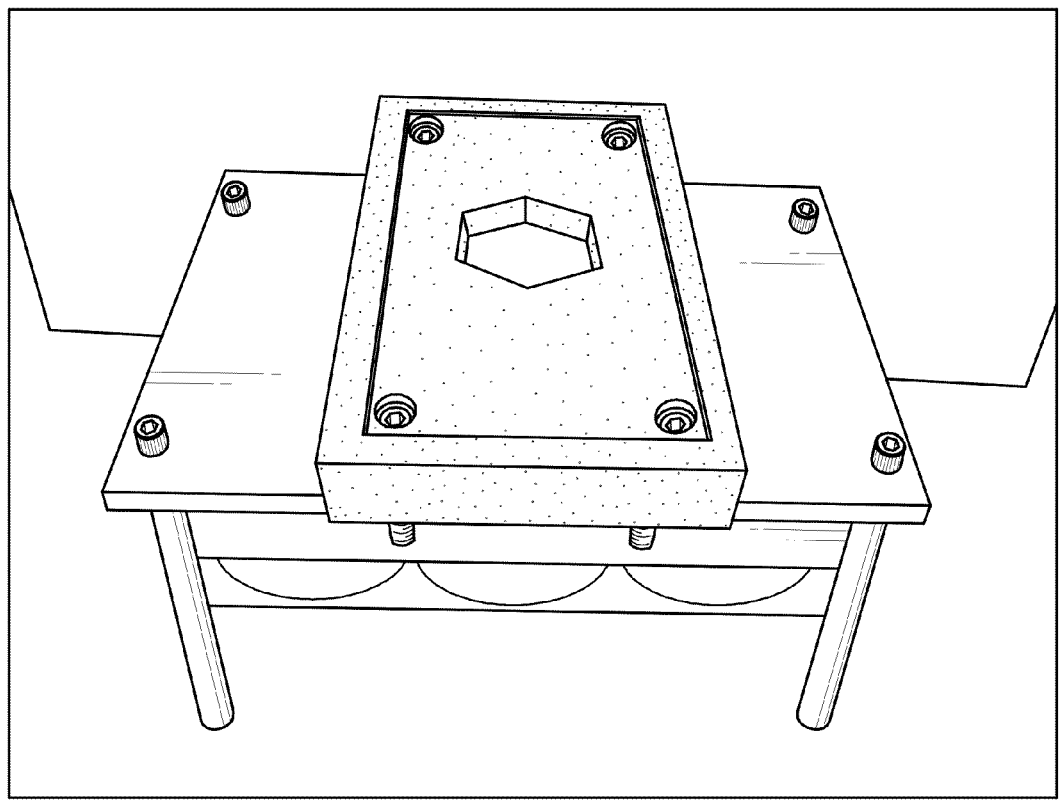
FIG. 11 is a representative illustration showing the set up of Alpha heat sinks with cooling plate surrounded by Styrofoam on top.

Thermal Shocked Procedure:

FIG. 11 is a representative illustration showing the set up of Alpha heat sinks with cooling plate surrounded by Styrofoam on top. As shown in FIG. 11, thermal shocked samples were placed on top of 2 Alpha Heatsinks and allowed to cool down following three different protocols:

Protocol Cooling Control: A subset of samples was surrounded in ice until samples were approximately 0° C. at a rate of <0.39° C./min. Proof of cooling concept samples are another subset of these samples were cooled in the same way and then irradiated as described above for approximately 7-15 seconds, until the samples reached 45-60° C.

Protocol Slow Cooling: A subset of samples was cooled down at a rate of 1.075° C./min until they reached a minimum temperature of −20° C. Then they were introduced into the incubator and allowed to be re-warm to 30° C. Slow Cooling, 1320 samples are another subset of these samples was cooled in the same way and then irradiated for approximately 2-4 seconds until a maximum temperature of 45° C. was reached.

Protocol Quick Cooling: A subset of samples was cooled down at a rate of 21.5° C./min until they reached a minimum temperature of −20° C. Then they were allowed to be re-warm to 30° C. in the incubator. Quick Cooling, 1320 samples are another subset of these samples was cooled in the same way and then irradiated for approximately 3-6 seconds until a maximum temperature of 45° C. was reached.

Standardized photographs were taken with Nikon CoolPix 3100 digital camera from 8 cm above the surface of the sample, 24 hours after the experiment and up to 7 subsequent days thereafter. Assessment of colony growth was made by converting standardized digital images into bitmap format, counting the amount of pixels per colony and converting this count to an average surface area in $mm^2$ using Microsoft™ Paint Program (Microsoft, Seattle, Wash.).

Figure 12:
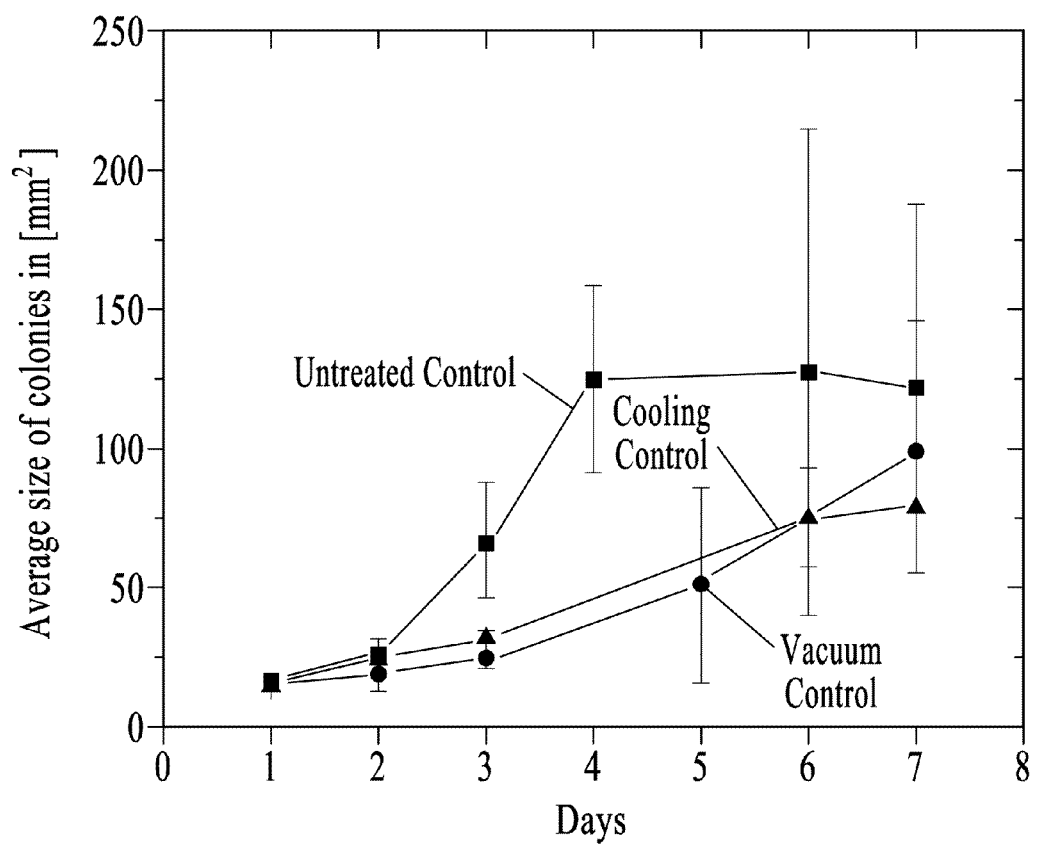
FIG. 12 is a representative chart showing a comparison of average size of control sample in $mm^2$.

Results:

FIG. 12 is a representative chart showing a comparison of average size of control sample in $mm^2$. In FIG. 12, squares indicate measurement of untreated control samples, circles indicate measurement of vacuum control samples and triangles indicate measurement of cooling control protocol samples. FIG. 12 shows preliminary results of the average growth rate and standard deviation of all control samples, which are those not irradiated. As shown in FIG. 12, the growth rate of the vacuum control samples and cooling control samples was slower than that of the untreated control samples. However, the trend of the vacuum control samples and cooling control samples toward the last days of this study seem to suggest that all control samples could have reached the same average size given long enough periods of time.

Figure 13:
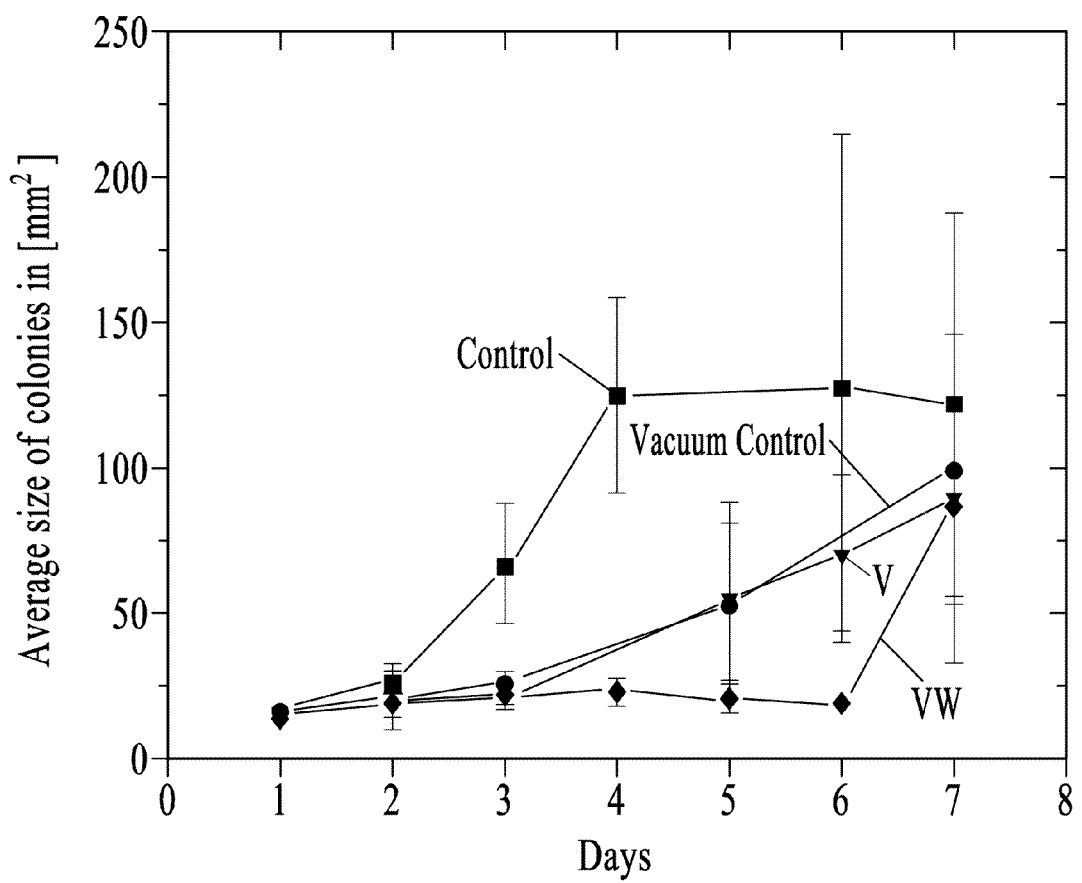
FIG. 13 is a representative chart showing a comparison of average size of colonies in $mm^2$ of four samples.

Vacuum Procedure (A) Results:

FIG. 13 is a representative chart showing a comparison of average size of colonies in $mm^2$ of four samples in the vacuum conditions (a) experiments. In FIG. 13, squares indicate measurement of untreated control samples, circles indicate measurement of vacuum control samples, upside town triangles indicate measurement of vacuum procedure without water dousing or hydration pre-procedurally samples (V) and diamonds indicate measurement of vacuum procedure after water dousing or hydration samples (VW). More specifically, the curve labeled "V" corresponds to the samples placed under vacuum, irradiated with 40-90 J, and left to grow. The curve labeled "VW" corresponds to those that were first doused or hydrated in water, placed in vacuum, and then irradiated with 40-90 J.

As shown in FIG. 13, while vacuum alone, as in vacuum control samples, seem to hamper the colony growth rate relative to untreated control samples, there was no significant difference between the vacuum control and (V) samples. Thus, irradiation alone does not appear to change the size of the colonies or growth rate once placed in vacuum. However, when the samples were doused with water and irradiated, as in (VW) samples, the growth rate was significantly suppressed for up until day 6, but for many of these samples, significant growth was observed by day 7, regardless of the energy input.

Figure 14A:
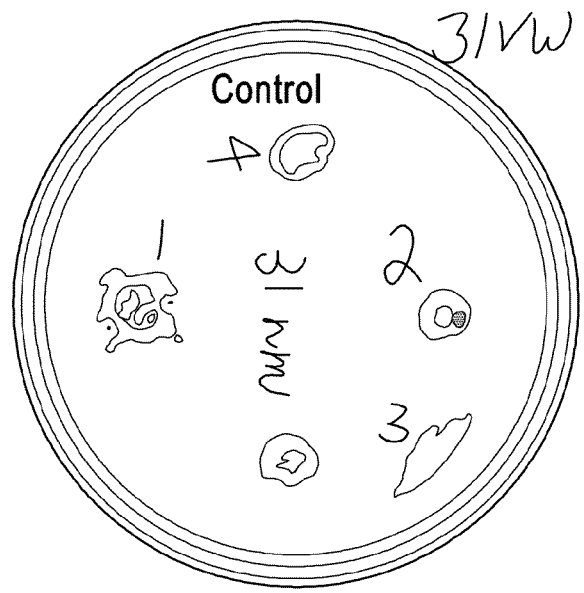
FIGS. 14A and 14B are representative graphics showing examples of medium affected by VW treatment.
Figure 14B:
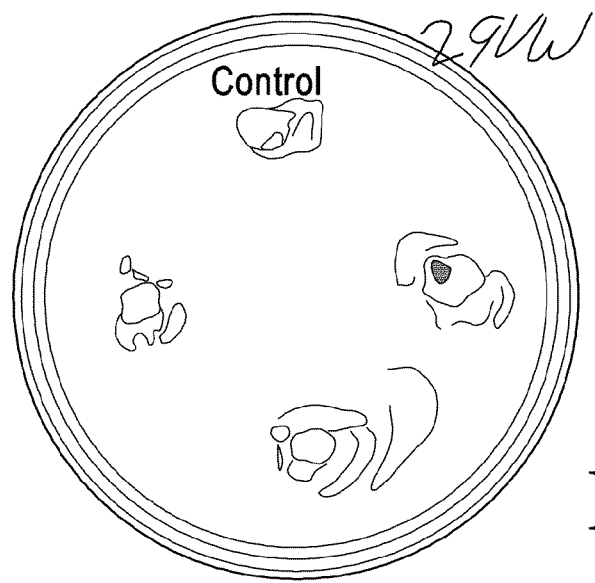

FIGS. 14A and 14B are representative illustrations showing examples of medium affected by (VW) treatment. FIG. 14A shows an example of normal medium after three days after (VW) treatment and FIG. 14B shows an example of medium that was adversely affected by the (VW) treatment shown in day three of post treatment. During the irradiation of many of the (VW) samples, it was observed that steam was formed and bubbles would form inside the medium and remained trapped for the duration of the experiment. The higher the energy input, the more steam and bubbles were produced. Also, a third of the Petri dishes used were affected in an unforeseen way. The consistency of the entire medium changed becoming thicker and grainy as shown in FIGS. 14A and 14B. This new medium greatly inhibited fungus growth.

Figure 15:
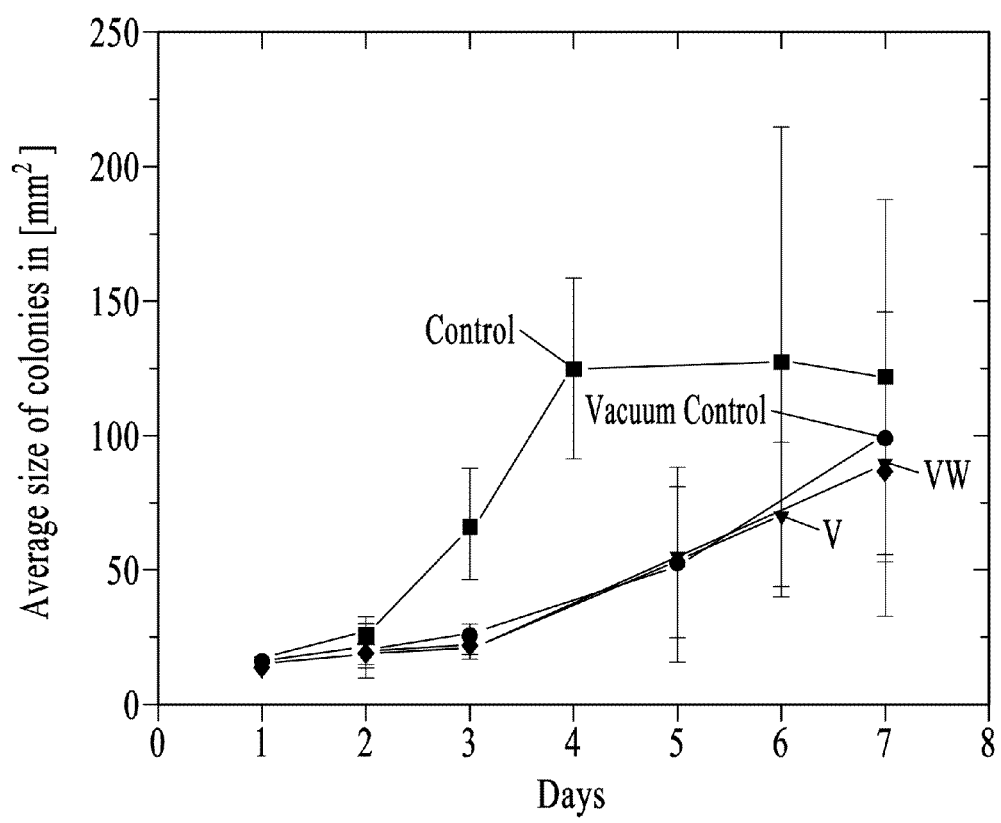
FIG. 15 is a representative chart showing a comparison of average size of colonies in $mm^2$ of four samples.

FIG. 15 is a representative chart showing a comparison of average size of colonies in $mm^2$ of four samples. When the Petri dishes that showed the thicker and grainy medium were removed from the analysis, the (VW) curve ended up matching the curves of the vacuum control and (V) samples, as best shown in FIG. 15.

Figure 16:
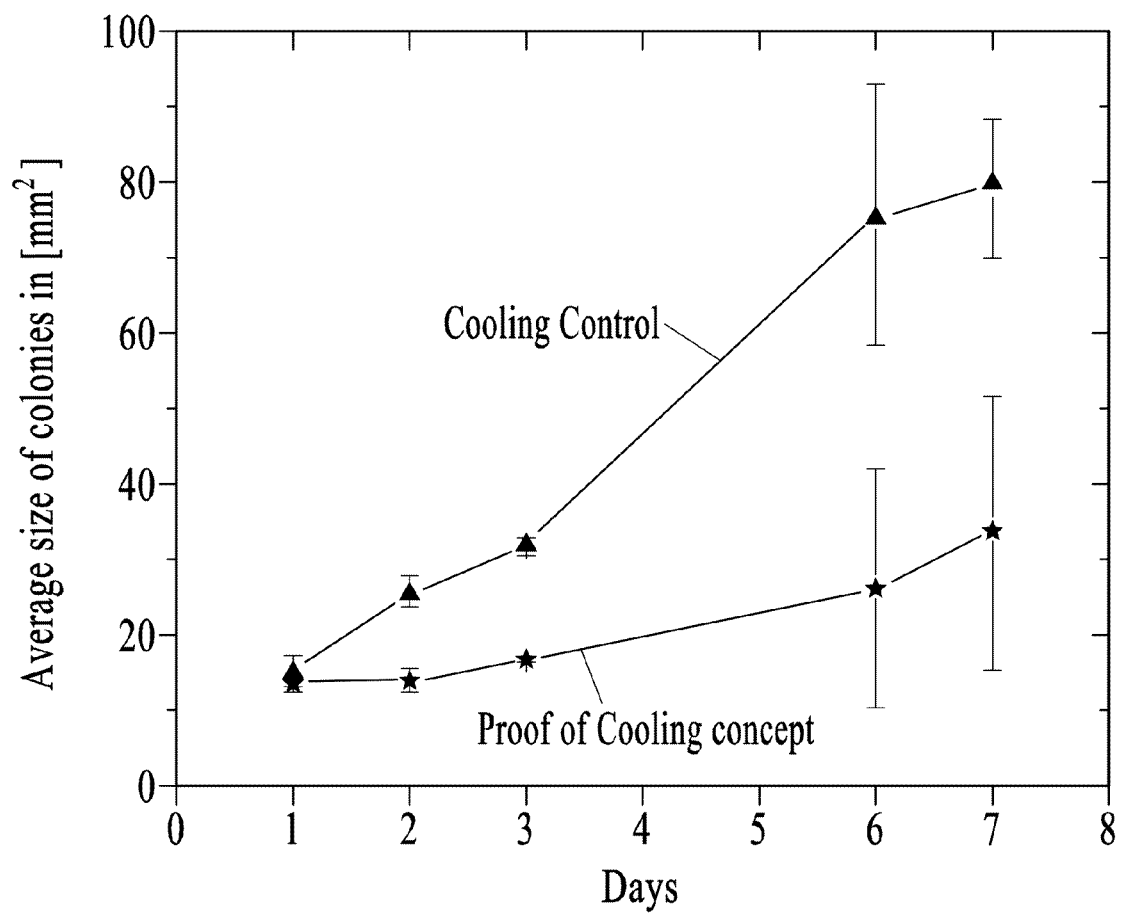
FIG. 16 is a representative chart showing a comparison of average size of colonies in $mm^2$ of two samples.

Thermal Shock Procedure (B) Results:

FIG. 16 is a representative chart showing a comparison of average size of colonies in $mm^2$ of two protocol cooling control samples. More specifically, triangles indicate measurement of protocol cooling control samples and stars indicate measurement of proof of cooling concept samples which were subjected to >100 J and the temperature 45-60° C. As shown in FIG. 16, this aggressive protocol proof of cooling concept was effective in hampering the growth of the colonies for all seven days. Only a few samples showed a small amount of growth over the week. It is unclear, however, if the effect on the growth rate is due to the temperature gradient, minimum and/or maximum temperature reached, or the total amount of energy administered by the laser. Clearly, this procedure would be unsuitable for clinical use due to the extreme temperatures involved.

Figure 17:
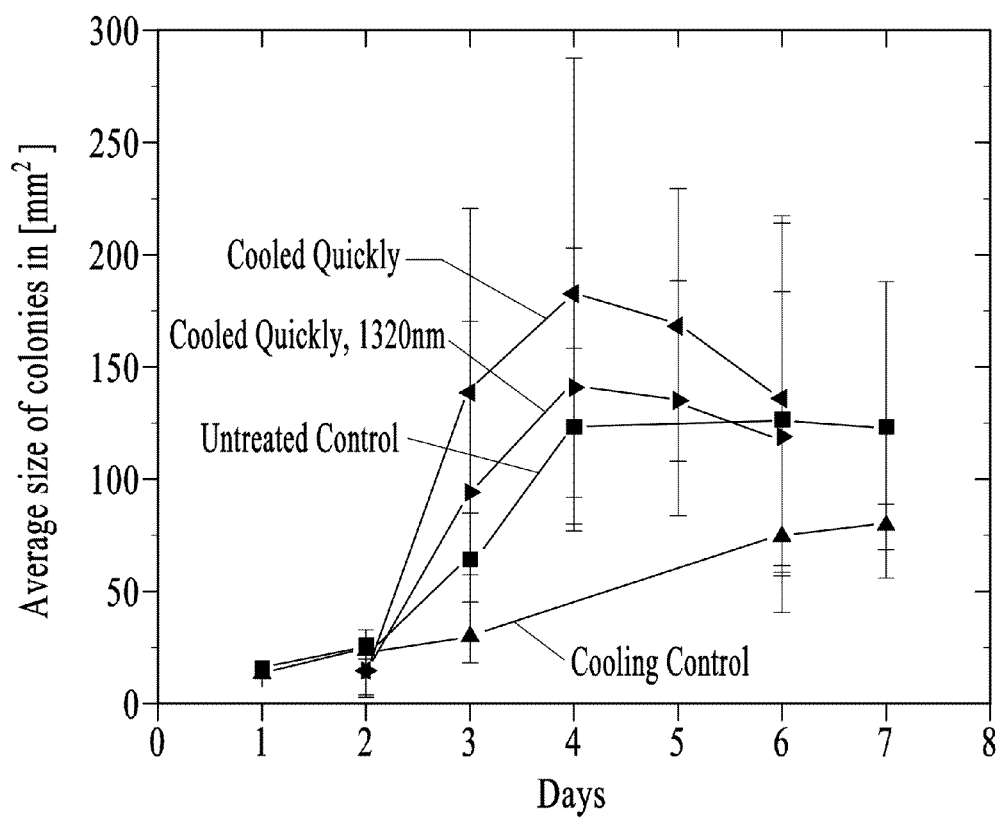
FIG. 17 is a representative chart showing a comparison of average size of colonies in $mm^2$ of four samples.
Figure 18:
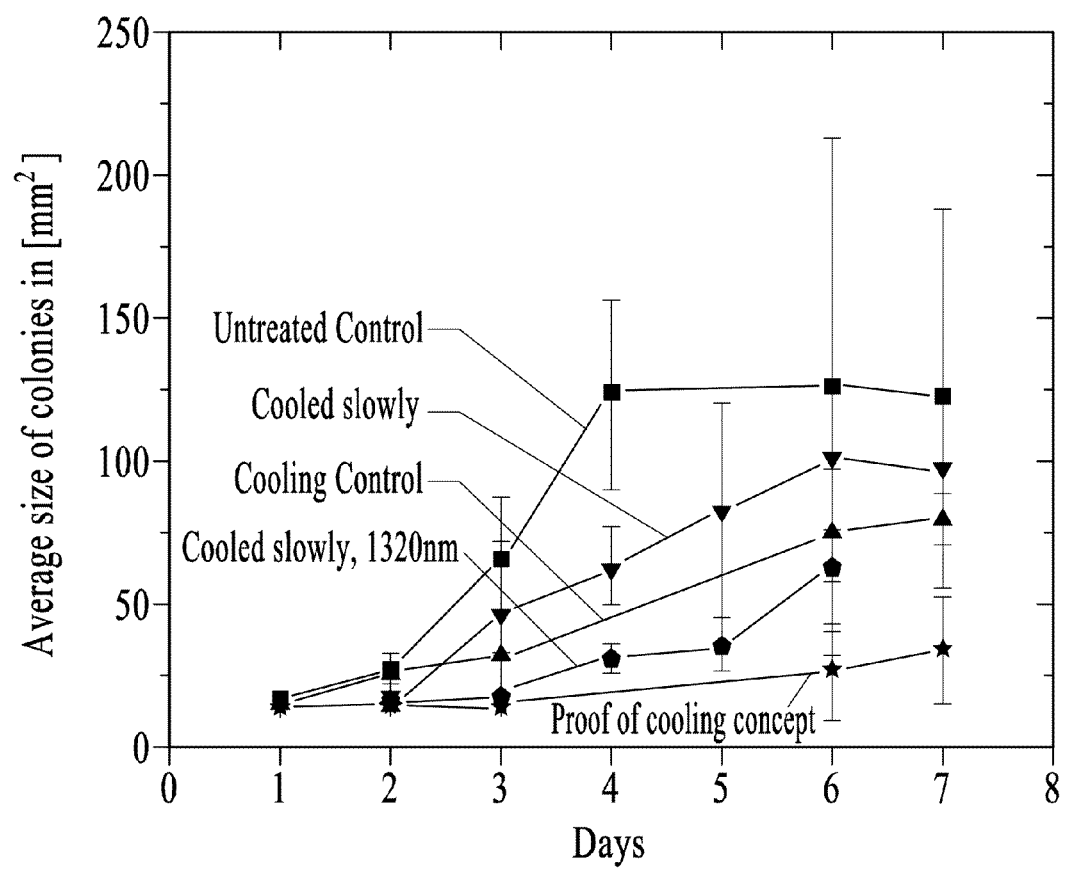
FIG. 18 is a representative chart showing a comparison of average size in $mm^2$ of a different set of four samples.

The results of the three cooling protocols with and without irradiation, along with the untreated and cooling controls are shown in FIGS. 17 and 18. More specifically in FIG. 17, squares indicate measurement of untreated control samples, triangles indicate measurement of cooling control samples, left facing triangles indicate measurement of protocol quick cooled with irradiation samples and right facing triangles indicate measurement of protocol quick cooled without irradiation samples. And more specifically in FIG. 18, squares indicate measurement of untreated control samples, triangles indicate measurement of cooling control samples, stars indicate measurement of procedure proof of cooling concept samples, hexagon indicate measurement of protocol slow cooled with irradiation samples and upside down triangles indicate measurement of protocol slow cooled without irradiation samples.

Several observations can be made based on these experiments:

1. Relative to the untreated controls, the slow cooling procedure both with and without irradiation demonstrated a slower growth rate and smaller average size;
2. Both the irradiated and non-irradiated samples that were quick cooled demonstrated at least the same if not higher growth rates than the untreated control;
3. Laser irradiated samples show a reduced growth rate relative to their non-irradiate counterparts;
4. Relative to the cooling control, the slow cooled samples that were not irradiated had larger then average colony sizes. On the other hand, the slow cooled and irradiated samples had smaller colony sizes. All three showed similar growth rates; and
5. The results that showed the slowest growth rate were the proof of cooling concept. The second slowest were the cooled slowly, irradiated samples.

Discussion:

Vacuum Condition Procedure (A):

The objective of using vacuum pressure in conjunction with laser irradiation was, amongst other purposes, to take advantage of the reduced boiling temperature of water and either make more efficient use of the heat imparted via the laser or reduce the fluence required for fungus necrosis. The standard dry samples were very dry and while not overly desiccated, they did not have much excess water to alter with the vacuum pressures. Dehydrated conidia, one of the main types of spores that *T. rubrum* uses to infect and reproduce, can resist up to 124° C. for up to 3 minutes while still remaining largely viable, as disclosed in Schmit, J. C. et al., "Biochemical genetics of *Neurospora crassa* conidial germination", Microbiology and Molecular Biology Review, 1976. Thus, making the vacuum system no more effective then simply irradiating the samples while under standard temperature and pressure initial conditions, as best shown in FIG. 13. As best shown in FIGS. 14A, 14B and 15, water dousing or hydration appeared to have an important effect at first, but its effectiveness seem to be correlated with inexplicable changes we observed in the media which, once removed, appeared to have no effect. One of the factors that needs to be highlighted is that vacuum alone appeared to hamper the growth rate of the colonies with little to no effect from irradiation when the samples with deformed medium were removed, as best shown in FIG. 15, which leads us to believe that humidity may be a very important factor. In 1976, Schmit proposed that conidia viability was affected by humidity. Storing conidia at 100% humidity killed the samples after only nine days at 22° C. Other works indicated that *Trichophyton mentagrophytes*, the other main dermatophytes related to onychomycosis, has a very narrow humidity range of 95-98% and that different levels of humidity are better or worse for different stages of *T. mentagrophytes*—high humidity is necessary for arthrospore formation but reduced humidity necessary for maturation, as disclosed in Knight, A. G. "The effect of temperature and humidity on the growth of *Trichophyton mentagrophytes* spores on human stratum corneum in vitro", Clin Exp Dermatol, 1976. 1: p. 159-162. While *T. mentagrophytes* and *T. rubrum* are not the same, they are similar enough to warrant further studies investigating the effect of humidity and spore creation and growth.

In relation to our experiments, humidity comes into question when the effects of the (VW) technique are studied. The energy imparted to the sample during (V) and (VW) techniques was the same as the initial experiments of simple irradiation of a dry or wet sample with no other environmental factors (data not shown). Even though the energy was the same, the vacuum pressure reduces the boiling temperature of the water and thus it was reached sooner. This boiling, while enclosed in the small vacuum chamber, produced steam that would raise the relative humidity of the environment. Samples that received more energy also created more steam which may have further inhibited the growth rate of the samples. It is also possible that the humidity reached fits within the narrow band necessary for the efficient production of arthrospores while also destroying the main section of the fungus, thus minimizing the thermal effect that the laser irradiation would have on the growth rate. The current experiments cannot differentiate the effect of energy, overall temperature, or humidity from the results of the growth rate or colony size, so this should be investigated further.

As discussed above, there were many effects to the medium that could also change the outcome of the results. The water when placed on the sample did not only soak up into the fungus, but it also surrounded the fungus even going so far as to filter through the medium to get underneath the sample or in the crevices at the edge of the Petri dish. While irradiating the sample, the area directly around the sample would also become heated, as well as the water trapped within or around the medium. This caused the medium to change. Sometimes small bubbles would form in the medium that could not dissipate. For one third of the cases the medium was irrevocably changed for unknown reasons which greatly inhibited fungus growth as seen by the change between FIGS. 11A and 11B.

Thermal Shock Procedure (B):

*T. rubrum* is incredibly resistant to many extreme environments including heat, cold, and dryness. Dormant conidia and arthrospores, which are considered the main way that *T. rubrum* spreads and stays alive, have been known to survive at 4° C. for at least three years, with no morphological changes or mutations, as disclosed by Sinski et al., "Effect of storage temperature on viability of *Trichophyton mentagrophytes* in infected guinea pig skin scales, Journal of Clinical Microbiology, 1979. 10(b): p. 841. They can also withstand −70° C. for up to six months with no significant morphological changes, according to Baker M et al. and Espinel-Ingroff et al. studies. *T. rubrum* has also been known to be extremely resistant to heat. Mature conidia can withstand 55° C. for ten minutes with no loss in viability and more than 90% of dehydrated conidia can resist up to 124° C. for as much as three minutes, as disclosed in Schmit, J. C.'s publication. Dropping the initial cooling temperature to −20° C. and then raising it quickly to 45° C. is well within the range that many of the conidia can withstand, however, the quick cooling and heating rates may expose the fungus to extreme conditions that it may not be able to withstand. Further studies are required to address this issue.

The proof of cooling concept worked well because the samples were brought above 55° C. in a small amount of time and the sample was not completely desiccated due to the medium that it was growing on, making it more susceptible to the heating process. But it also explains why even those samples were not completely destroyed. All it takes is one viable conidia spore to create a whole new colony and the current procedure that is bounded by clinical pain boundaries is not enough to kill the entire sample. The samples that were more significantly affected out of the clinical temperature samples were the ones that were cooled slowly and then immediately irradiated to 45° C. The growth rate was about the same as the cooling control but the sample sizes were smaller overall for the first half of the week. Later, growth rate sped up and growth continued as normal. This may be an indicator that more of the sample was in a dormant stage due to the lower initial temperatures but that it was able to sufficiently recover and continue its growth. Multiple treatments following the same procedure or the introduction of topical or oral antifungal medications after initial thermal shock may continue to hamper and possibly eliminate the fungal growth.

The effects that were seen may also be due to the damage to the medium more than the sample itself. Freezing the Petri dish had the possibility of shrinking the entire plate of medium due to its high water content thereby inherently changing the fungi's ability to grow. For this experiment the samples that were dropped to only 0° C. were frozen as one dish while the samples that were reduced to −20° C. were frozen individually. Therefore, the shrinkage was only a possibility for the 0° C. experiments and not for the revised experiments thus mitigating the medium problem.

Conclusions

Our results indicate that the vacuum condition (a) approach hampers the growth rate of fungi colonies relative to untreated control samples, especially the combination of water dousing or hydration prior to laser irradiation under vacuum conditions. Thermal shock (b) approach can also reduce the growth rate of fungi colonies when slow cooling is applied followed by rapid laser irradiation, while quick cooling preceding laser irradiation shows little effect.

Exposing fungi to vacuum alone appears to deter the fungus growth rate, even without laser irradiation. However, when fungus water dousing precedes laser irradiation, the growth rate is hampered even more. Overall, the vacuum samples showed some promise in that they did inhibit the growth of the samples but the results were not consistent and it is not entirely clear as to whether it is the fungus or the medium which is greater affected. Further studies must be done to distinguish the effects of humidity, as well as the effect of both thermal shock and vacuum combined and in multiple applications.

Most of the cooling results showed minimally effective at inhibiting the growth rate of *T. rubrum*. The best results so far are contained within the protocol proof of cooling concept samples but it was unclear whether or not it was the temperature gradient, maximum temperature, or amount of energy that had the dominant effect. The protocol cooling experiments that dropped the initial cooling temperature to −20° C. recreated the same temperature gradient as the proof of cooling concept samples but the results were universally worse producing a faster growth rate and larger sample size. This ruled out the temperature gradient, thus leaving the maximum temperature or the total amount of energy as the only feasible parameters to explain the difference. While the quick cooling samples at −20° C. produced unfavorable results, the results of the slow cooled, 1320 samples were promising. They reduced the growth rate and colony size beyond that of the cooling control while still staying within suitable temperature ranges for clinical use. The combination of thermal shock with vacuum or topical chemicals to improve upon the current results should be investigated in the future.

Since laser heating is still the underlying procedure, studies were initiated aimed at characterizing optically, both healthy and diseased human nails.

Figure 19A:
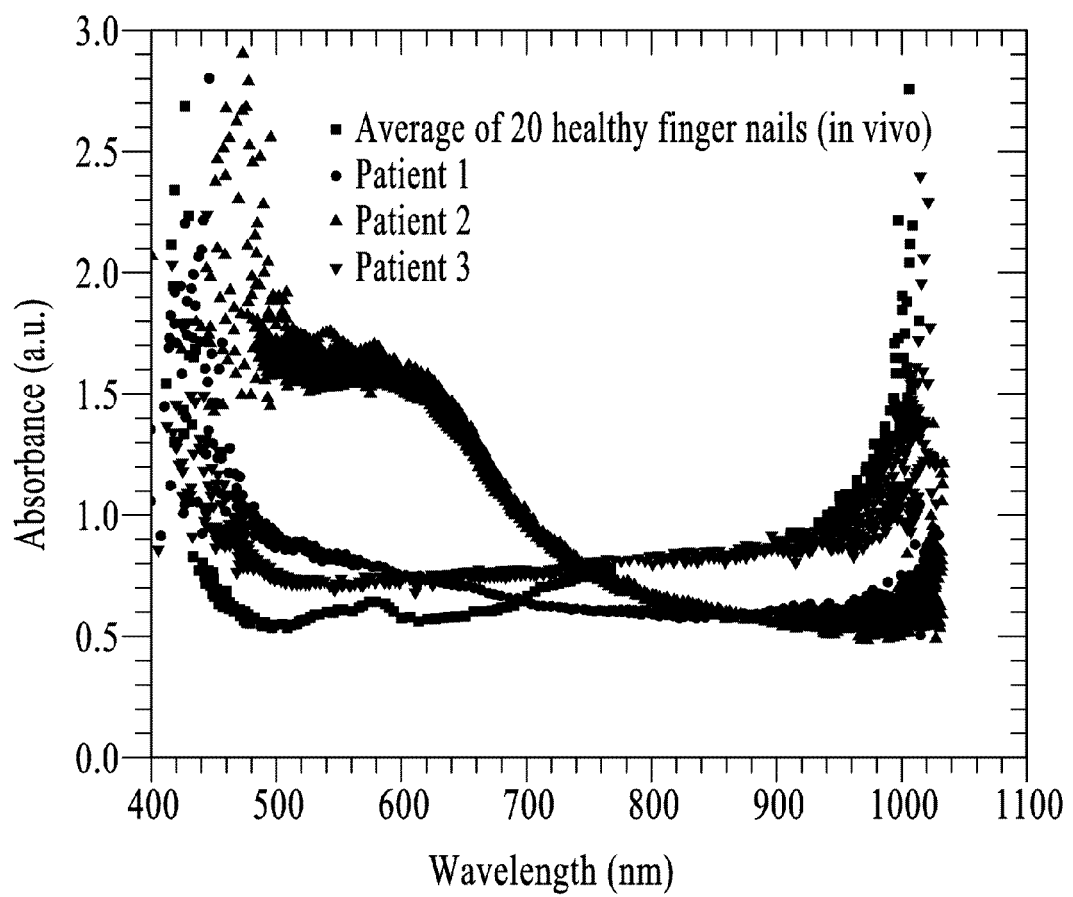
FIG. 19A is a representative graphic showing the appearance of 20 healthy in-vivo finger nails.

FIG. 19A shows the absorbance spectra of the average of twenty healthy finger nails and three diseased human toe nails, the apparent absorbance was obtained from reflectance measurements as the negative of the logarithm base 10 of the reflectance. These optical measurements could be used to determine which wavelength would be better absorbed by the diseased nail and use that wavelength to increase the nails temperature thus affecting more of the fungus overall and having a better chance to affect the fungus trapped on the edges of the nail or inside the nail itself. The difference in the absorbance spectrum between diseased nails could relate to different subtypes of onychomycosis or different stages of the disease, a nail in an advanced stage of onychomycosis is thicker and more opaque than a nail in an earlier stage of the disease, this thickness and opaqueness can be seen as an increase in absorbance in the visible portion of the spectrum as can be seen in the absorbance spectrum of Patient 2 in FIG. 19A.

Figure 19D:
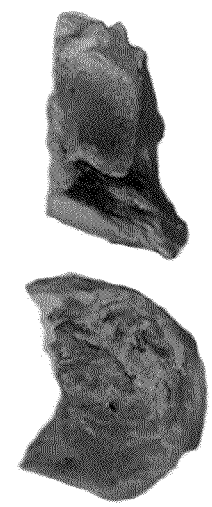
FIGS. 19B, C and D are representative graphics showing the appearance of diseased, ex-vivo toe nails, with FIG. 19B corresponding to circles, with FIG. 19C corresponding to triangles up, and with FIG. 19D corresponding to triangles down.
Figure 19C:
Figure 19B:
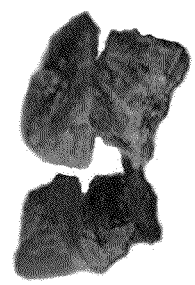

FIGS. 19 B, C and D are representative graphics showing the appearance of diseased, ex-vivo toe nails, with FIG. 19B corresponding to circles, with FIG. 19C corresponding to triangles up, and with FIG. 19D corresponding to triangles down.

Experiment IV (March 2010)

Summary:

In this paper, we present preliminary results using the CoolTouch® 1320 nm mid-infrared CoolBreeze™ laser on patients to treat toenails that have demonstrated dermatophyte infections resulting in onychomycosis. Fungal infection was determined by the investigator pre-treatment. Toes were treated a minimum of two times at separate sessions with a minimum of 4-week intervals. There were 38 patients with a total of 54 toes treated. All subjects tolerated the treatments without anesthesia with one subject reporting an adverse event complaining of a localized, sharp pain like sensation that resolved within two months. Forty-three out of 54 (79.6%) toes treated showed a measurable increase in clear nail area. Improvement in the areas of clear nail growth was measured from 30 to 180 days post the final treatment.

Background:

Organisms that cause onychomycosis can invade both the nail bed and the nail plate. Dermatophytoses of the fingernails and toenails, in contrast to those at other body sites, are particularly difficult to eradicate with drug treatment. This is the consequence of factors intrinsic to the nail—the hard, protective nail plate, sequestration of pathogens between the nail bed and plate, and slow growth of the nail, as well as of the relatively poor efficacy of the early pharmacologic agents.

Study Rationale:

The efficacy of current treatment options, including topical, oral, mechanical and chemical therapies or a combination of these modalities is low. Topical drug treatment for onychomycosis is not usually successful because the drugs are unable to penetrate the nail plate and rapid recurrence can occur after discontinuing use. Oral antifungal agents are more effective although more toxic with a significant risk of liver toxicity, prolonged loss of taste, and life threatening drug interactions. Fungal resistance can occur when the oral antifungal agents are used on a long-term basis. Topically applied antifungal drugs may work somewhat better adjunctive to surgical removal or chemical dissolution of the nail plate. Yet, this often ineffective and traumatic procedure leaves the subject without a nail for months at risk for re-infection. The purpose of this study is to evaluate feasibility of the use of the CoolTouch® CT3P CoolBreeze™ laser to treat distal onychomycosis of the toenails.

Device Description:

The CoolTouch® CT3P CoolBreeze™ 1320 nm 18W pulsed Nd:YAG laser is an FDA (K043046) cleared device and is indicated for use in dermatology for incision, excision, ablation and vaporization with hemostasis of soft tissue.

The unique handpiece design of the CoolTouch® laser allows the operator to maintain a constant distance from the area to be treated resulting in constant and uniform energy delivery. Treatment spot size is adjustable from 3 mm to 10 mm allowing pre-selection of the optimal spot size for the nail being treated. The energy delivered to the toenail can be adjusted by the selecting the desired level of watts (1.5 W to 12 W) with a push of a single control panel key. The CT3P CoolBreeze™ laser has a unique thermal sensing mechanism design to control the amount of energy delivered to the toenail by presetting the desired end target temperature. In addition, patient comfort is assured by a spray of a cooling agent when the target temperature is reached. Unlike other laser systems, having the fiber enclosed and terminated in the handpiece means that the fiber does not need cleaving during or after the laser procedure.

Study Design:

Thirty-eight volunteer subjects were recruited in a private podiatric practice. All of the subjects signed informed consent forms. Subjects were of either sex, greater than 18 years of age and determined to have subungual onychomycosis by the primary investigator.

Subjects were excluded from the study if they were pregnant, had a history of any treatment for onychomycosis within 3 months of the study enrollment date, had prior skin treatment with a laser or other devices on the same treated areas within 6 months of initial treatment, had prior use of topical medications (especially corticosteroids) in the treatment area within 2 weeks of the study period or systemic corticosteroids within 6 months of study enrollment or during the course of the study. Any condition which, in the investigator's opinion, would make it unsafe; for the subject or for the study personnel; to participate in this research study.

Each treated area was cleaned before treatment using alcohol-free agents to ensure that any perfumes, cosmetics, or lotions were removed. Nails were debrided pretreatment. Photographs for the evaluation were taken pre-treatment. The laser procedures were performed in the identified treated areas and all laser settings, spot size, watts, target temperature, cooling duration and total energy delivered were recorded at each laser treatment session. Patients were instructed to follow-up with daily foot care, applying an antifungal cream and scrubbing the toenails with soap/bleach solution, such as Pedinol®.

In addition, at the four and twelve and twenty-six week follow-up visits the following parameters were assessed and documented:
1. Photography of treated toe and foot;
2. KOH testing for dermatophyte infection;
3. Subject's self-reported level of pain or discomfort;
4. Subject's satisfaction with treatment;
5. Subject's self-reported level of improvement; and
6. Adverse events will be assessed, with continued monitoring and evaluation at subsequent visits.

Results:

Discomfort and pain levels were assessed immediately post treatment #1 and treatment #2 and at 1 week post last laser treatment. Pain and discomfort were graded on a 1 to 5 scale by the patient with 1 being no pain and 5 as severe pain Immediately post laser treatment #1, patients reported a cumulative value of 1.8; post treatment #2 the calculated value was 1.9. Perceived pain and discomfort was reported to be between no pain and slight pain with no patients reporting a value higher than 3 (mild pain).

The investigator reported, by visual assessment, a positive response demonstrating a 79.6% increase in clear nail growth as compared to baseline photographs in the group of laser treated toes. Patient satisfaction (1—not satisfied to 5—extremely satisfied) in the reporting group at week 4 was 3.4, at week 12 the reported value increased to 3.6 resulting in a satisfaction level between satisfied to very satisfied. This patient subset showing improvement; as determined by the investigator; reported a 100% agreement with this determination.

Only one adverse event was reported; a localized, sharp pain like sensation in the large toe that resolved within two months.

Discussion:

In this early assessment of the CoolTouch® CT3P CoolBreeze™ 1320 nm laser for the treatment of onychomycosis, positive results are seen in clear nail plate increase in nearly 80% of the toenails treated. Unlike prior drug studies, no attempt was made to narrow the cohort of patients by selective eliminating those patients with proximal infections and nail matrix involvement, the very difficult to treat patient group usually non-responsive to pharmacologic agents. A two or three laser treatment regimen allows much higher patient compliance with the treatment protocol, very high patient safety with minimal or no side effects. Documented high patient satisfaction with minimal patient reported pain or discomfort suggests a safe and tolerable procedure. In addition, using the CoolTouch® CT3P CoolBreeze™ laser the procedure can be performed in less than 15 minutes; total treatment time for both feet and all toes with multiple passes; and allows effective utilization of valuable physician time.

Improved nail clearing demonstrated with these preliminary results support the hypotheses that the 1320 nm wavelength, using controlled energy delivery and a cooling spray is an effective treatment modality that inhibits or destroys the dermatophyte pathogens that cause onychomycosis resulting in high patient satisfaction. These findings strongly suggest comparable results with the other studies published and allow for greater physician choice in the equipment needed for the treatment of onychomycosis.

Concurrently-owned U.S. Pat. No. 5,820,626 entitled COOLING LASER HANDPIECE WITH REFILLABLE COOLANT RESERVOIR, U.S. Pat. No. 5,976,123 entitled HEAT STABILIZATION, U.S. Pat. No. 6,451,007 entitled THERMAL QUENCHING OF TISSUE, U.S. Pat. No. 7,122,029 entitled THERMAL QUENCHING OF TISSUE, U.S. Pat. No. 6,413,253 entitled SUBSURFACE HEATING OF MATERIAL, U.S. Pat. No. 6,273,885 entitled HANDHELD PHOTOEPILATION DEVICE METHOD and U.S. Pat. No. 7,217,265 entitled TREATMENT OF CELLULITE WITH MID-INFRARED RADIATION are hereby incorporated herein in their entireties in regards to their teaching of methods and apparatus for cryogenic cooling as part of an overall medical, dermatological and/or aesthetic treatment.

Unless defined otherwise, all technical and scientific terms used herein have the same meaning as commonly understood by one of ordinary skill in the art to which the present invention belongs. Although any methods and materials similar or equivalent to those described can be used in the practice or testing of the present invention, the preferred methods and materials are now described. All publications and patent documents referenced in the present invention are incorporated herein by reference.

While the principles of the invention have been made clear in illustrative embodiments, there will be immediately obvious to those skilled in the art many modifications of structure, arrangement, proportions, the elements, materials, and components used in the practice of the invention, and otherwise, which are particularly adapted to specific environments and operative requirements without departing from those principles. The appended claims are intended to cover and embrace any and all such modifications, with the limits only of the true purview, spirit and scope of the invention.

We claim:

1. A method for treatment of microbial infection of human toenails, the method comprising the steps of:
treating a subsurface layer of skin with a source of electromagnetic energy in the infrared range sufficient to cause stimulation of an immune response without thermal damage to the surface layer, in conjunction with applying and anti-microbial agent directly to the upper surface of the nail, thereby improving treatment efficiency; and
using a vacuum attachment over the infection site to reduce the pressure around the infected site and thereby reduce the effective boiling temperature of water located in the surrounding tissue, thereby improving treatment efficiency and/or reducing associated patient pain.

2. The method of claim 1 wherein the treatment with electromagnetic energy is repeated serially with more than one day between any successive treatments.

3. The method of claim 1, further comprising the steps of sequentially and repeatedly irradiating the infected portion with infrared radiation and cooling the infected portion such that heat and cold alternatingly penetrates to the site of the infection in order to inactivate the pathogen.

4. The method of claim 3, further comprising the step of using non-contact thermal measurement of the infected site to automatically control either or both the heating and the cooling of the site.

5. The method of claim 1, further comprising the step of treating the site of infection with GNP or other particle seeds to create a rapid and violent thermoelastic expansion or cavitation of the tissue surrounding the microbial infection during infrared radiation exposure, thereby improving treatment efficiency.

6. The method of claim 1, further comprising the step of using temporary modification of the optical properties of the toe skin, thereby reducing or increasing the incidence of back scattering/absorption.

7. The method of claim 1 further comprising the step of hydrating the nail with warm water.

8. The method of claim 1 wherein the step of irradiating the infected portion with infrared radiation is performed using laser energy having a wavelength between about 1200 nm and about 2000 nm.

9. The method of claim 1 wherein the step of irradiating the infected portion with infrared radiation is performed using laser energy having a wavelength of about 1320 nm.

10. The method of claim 1 wherein the step of irradiating the infected portion with infrared radiation is performed using laser energy having a wavelength between about 1450 nm and about 1550 nm.

11. The method of claim 1 wherein the step of irradiating the infected portion with infrared radiation is performed using laser energy having a wavelength of about 1470 nm.

12. The method of claim 1 further comprising the step of cooling with a liquid or gas applied directly to the target.

13. The method of claim 1 further comprising the step of applying liquid or gas directly to the infected portion, the liquid or gas containing one of more of the following: pain reducing agent, antifungal agent, anti-irritant agent, antimicrobial agent, antibiotic agent, antiseptic agent, disinfectant agent.

14. The method of claim 1 further comprising the steps of inducing mechanical damage to the site of the microbial infection by applying low pressures and temperatures below the threshold for photothermal damage.

15. The method of claim 1, further including the step of using pulsed radiation with a wavelength that is selectively absorbed by the microbes and with a pulse length that is chosen to match the thermal diffusion properties of the microbe.

* * * * *